US007264799B2

(12) United States Patent
Bennett et al.

(10) Patent No.: US 7,264,799 B2
(45) Date of Patent: Sep. 4, 2007

(54) USE OF HEPARINASES TO DECREASE INFLAMMATORY RESPONSE

(75) Inventors: D. Clark Bennett, Montreal (CA); Elizabeth Cauchon, Montreal (CA); Dominique Fink, Montreal (CA); Brigette Grouix, Montreal (CA); Ariane Hsia, Montreal (CA); Pamela Danagher, Montreal (CA); Joseph F. Zimmermann, Montreal (CA)

(73) Assignee: BioMarin Pharmaceutical Inc., Novato, CA (US)

( * ) Notice: Subject to any disclaimer, the term of this patent is extended or adjusted under 35 U.S.C. 154(b) by 0 days.

(21) Appl. No.: 11/357,967

(22) Filed: Feb. 22, 2006

(65) Prior Publication Data

US 2006/0140928 A1 Jun. 29, 2006

Related U.S. Application Data

(63) Continuation of application No. 11/118,477, filed on May 2, 2005, now abandoned, which is a continuation of application No. 08/722,659, filed on Sep. 27, 1996, now abandoned.

(60) Provisional application No. 60/004,622, filed on Sep. 29, 1995.

(51) Int. Cl.
*A61K 38/51* (2006.01)
*C12N 9/88* (2006.01)

(52) U.S. Cl. .................. 424/94.5; 424/94.1; 424/810; 435/232; 514/2

(58) Field of Classification Search ............... 424/94.1, 424/94.5; 514/2
See application file for complete search history.

(56) References Cited

U.S. PATENT DOCUMENTS

| 4,179,337 | A |   | 12/1979 | Davis et al. |
| 5,169,772 | A |   | 12/1992 | Zimmerman et al. |
| 5,340,800 | A |   | 8/1994 | Liu et al. |
| 5,362,641 | A |   | 11/1994 | Fuks et al. |
| 5,567,417 | A |   | 10/1996 | Sasisekharan et al. |
| 5,714,376 | A |   | 2/1998 | Sasisekharan et al. |
| 5,789,182 | A |   | 8/1998 | Yayon et al. |
| 5,997,863 | A | * | 12/1999 | Zimmermann et al. ..... 424/94.5 |

FOREIGN PATENT DOCUMENTS

| WO | 88/05301 | 7/1988 |
| WO | WO-91/07760 | 5/1991 |
| WO | WO-95/00171 | 1/1995 |

OTHER PUBLICATIONS

Bargatze et al., "Rapid G Protein-regulated Activation Event Involed in Lymphocyte Binding to Hight Endothelian Venules" The Journal of Experimental Medicine, vol. 178, pp. 367-373 (1993).
Bohn et al., "Fragmentation of Heparin by Enzymes from Newly Isolated Microorganisms" Drug Res. 41(1), Nr. 4, pp. 456-460 (1991).
Brach et al., "Leukotriene $B_4$ Transcriptionally Activates Interleukin-6 Expression Involving NK-$_x$B and NF-IL6*" Eur. J. Immunol., vol. 22, pp. 2705-2711, (1992).
Butcher, "Leukocyte-Endothelian Cell Recognition: Three (or More) Steps to Specificity and Diversity" Cell, 67, pp. 1033-1036 (1991).
Carlos et al., "Leukocyte-Endothelial Adhesion Molecules" Blood, vol. 84, No. 7, pp. 2068-2101 (1994).
Carlos et al., "Membrane Proteins Involved in Phagocyte Adherence to Endothelium" Immunol. Rev., No. 114,pp. 5-28 (1990).
Cohen et al., "Nonchromosomal Antibiotic Resistance in Bacteria: Genetic Transformation of *Escherichia coli* by R-Factor DNA*" Proc. Natl. Acad. Sci., vol. 69, No. 8, pp. 2110-2114 (1972).
Delgado et al., "The Uses and properties of PEG-Linked Proteins" Critical Rev. Ther. Drug Carrier Syst. vol. 9, Nos. 3-4, pp. 249-304 (1992).
Dustin et al., "Induction by IL 1 and Interferon-γ: Tissue Distribution, Biochemistry, and Function of a Natural Adherence Molecule (ICAM-1)[1]" J. Immunol., vol. 137, No. 1, pp. 245-254 (1986).
Ebisawa et al., "Eosinophil Transendothelial Migration Induced by Cytokines" J. Immunol., vol. 149, No. 12, pp. 4021-4028 (1992).
Finn et al., "Interleukin-8 Release and Neutrophil Degranulation After Pediatric Cardiopulmonary Bypass" J. Thorac. J. Surg., vol. 105, No. 2, pp. 234-241 (1993).
Galliher et al., "Heparinase Production by Flavobacterium Hepanium" Appl. Environ. Microbiol., vol. 41, No. 2, pp. 360-365 (1981).
Hanahan et al., "Platelet Activating Factor: A Biologically Active Phosphoglyceride" Ann. Rev. Biochem., vol. 55, pp. 283-509, (1986).
Harlan, "Leukocyte Adhesion Deficiency Syndrome: Insights into the Molecular Basis of Leukocyte Emigration" Clin. Immunol. Immunopath., vol. 67, No. 3, pp. S16-S24, (1993).
Hoogewerf et al., "CXC Chemokines Connective Tissue Activating Peptide-III and Neutrophil Activating Peptide-2 are Heparin/Heparan Sulfate-degrading Enxymes*" J. Biol. Chem., vol. 270, No. 7, pp. 3268-3277 (1995).

(Continued)

*Primary Examiner*—Christina Chan
*Assistant Examiner*—F. Pierre VanderVegt
(74) *Attorney, Agent, or Firm*—Marshall, Gerstein & Borun LLP

(57) ABSTRACT

Heparinase enzymes can be used as a medical treatment to reduce localized inflammatory responses. Treatment of activated endothelium with heparinase inhibits leukocyte rolling, adhesion and extravasation. Most of the heparin and heparan sulfate on endothelial cell surfaces and in basement membranes is degraded by exposure to heparinase. In addition, immobilized chemokines, which are attached to heparin/heparan sulfate on activated endothelium are solubilized by heparinase digestion. Heparinase can be infused into the vascular system to inhibit accumulation of leukocytes in inflamed tissue and decrease damage resulting from localized inflammations. Targeting of heparinase to activated endothelium can be accomplished through localized administration and/or use of genetically engineered heparinase containing endothelium ligand-binding domains.

8 Claims, 19 Drawing Sheets

OTHER PUBLICATIONS

Figure 1:
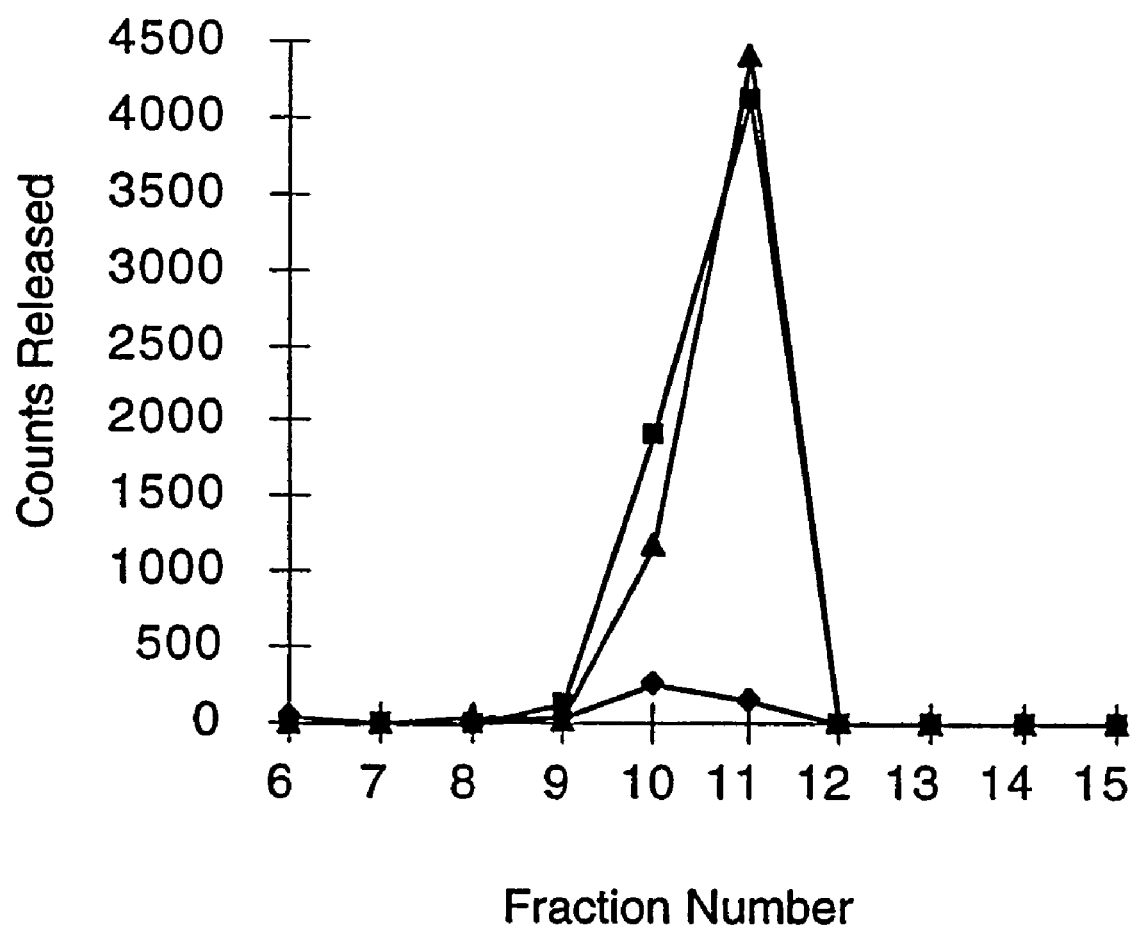

Hoover et al., "Leukotriene $B_4$ Action on Endothelium Mediates Augmented Neutrophil/Endothelial Adhesion" Proc. Natl. Acad. Sci. USA, vol. 81, pp. 2191-2193 (1984).

Huber et al., "Regulation of Transendothelial Neutrophil Migration by Endogenous Interleukin-8" Science, vol. 254, pp. 99-102 (1991).

Huber et al., "Disruption of the Subendothelial Basement Membrane During Neutrophil Diapedesis in an In Vitro Construct of a Blood Vessel Wall" J. Clin. Invest., vol. 83, pp. 1122-1136 (1989).

Hughes et al., "Role of Leukotriene $B_4$ in the Pathogenesis of Hepatic Ischemia-Reperfusion Injury in the Rat" Prost. Leuk. Essent. F. A., vol. 45, pp. 113-119 (1992).

Jeannin et al., "Histamine Induces Interleukin-8 Secretion by Endothelial Cells" Blood, vol. 84, No. 7, pp. 2229-2233 (1994).

Jutila et al., "Function and Regulation of the Neutrophil Mel-14 Antigen in Vivo: Comparison With LFA-1 and MAC-1[1]" J. Immunol., vol. 143, No. 10, pp. 3318-3324 (1989).

Kishimoto et al., "Neutrophil Mac-1 and MEL-14 Adhesion Proteins Inversely Regulated by Chemotactic Factors" Science, vol. 245, vol. 1238-124 (1989).

Kuijpers et al., "Neutropil Migration Across Monolayers of Cytokine-Prestimulated Endothelial Cells: A Role for Platelet-Activating Factor and IL-8" J. Cell Biol., vol. 117, No. 3, pp. 565-572 (1992).

Lasky, "Combinatorial Mediators of Inflammation?" Current Biol., vol. 3, No. 6, pp. 366-368 (1993).

Ley, et al., "Sialylated O-Glycans and L-Selectin Sequentially Mediate Myeloid Cell Rolling In Vivo" Blood, vol. 85, No. 12, pp. 3727-3735 (1995).

Lindemann, et al., "Granulocyte-Macrophage Colony-Stimulating Factor Induces Cytokine Secretion by Human Polymorphonuclear Leukocytes" J. Clin. Invest., vol. 83, pp. 1308-1312 (1989).

Lindemann et al., "Granulocyte-Macrophage Colny-Stimulating Factor Induces Interleukin 1 Production by Human Polymorphonuclear Neutrophils[1]" J. Immunol., vol. 140, No. 3, pp. 837-839 (1988).

Lo et al. "Endothelial-Leukocyte Adhesion Molecule 1 Stimulates the Adhesive Activity of Leukocyte Integrin CR3 (CD11b/CD18, Mac-1, $\alpha_m\beta_2$)" J. Exp. Med., vol. 173, pp. 1493-1500 (1991).

Lohse et al., "Purification and Characterization of Heparin Lyases from Flavobacterium heparinum*" J. Biol. Chem., vol. 267, No. 34, pp. 24347-24355 (1992).

Lorant et al., "Coexpression of GMP-140 and PAF by Endothelium Stimulated by Histamine or Thrombin: A Juxtacrine System for Adhesion and Activation of Neutrophils" J. Biol. Chem., vol. 115, No. 1, pp. 223-234 (1991).

Lowell, et al., "Proteosome-Lipopeptide Vaccines: Enhancement of Immunogenicity for Malaria CS Peptides" Science, vol. 240, pp. 800-802 (1988).

Lu, et al., "Pegylated Peptides I: Solid-Phase Synthesis of $N^\alpha$-Pegylated Peptides Using Fmoc Strategy" Pept. Res. Vo. 6, No. 3, 140-146 (1993).

Lukacs, et al., "Interleukin-1 Receptor Antagonist Blocks Chemokine Production in the Mixed Lymphocyte Reaction" Blood, vol. 82, No. 12, pp. 3668-3674 (1993).

Luscinaskas et al., "Inn Vitro Inhibitory Effect of IL-8 and Other Chemoattractants on Neutrophil-Endothelial Adhesive Interactions[1]" J. Immunol., vol. 149, No. 6, pp. 2163-2171 (1992).

Maccarana, et al., "Minimal Sequence in Heparin/Heparan Sulfate Required for Binding of Basic Fibroblast Growth Factor*" J. Biol. Chem., vol. 268, No. 32, pp. 23898-23905 (1993).

Matsushima, et al., "Interleukin-8 and MCAF: Nevel Leukocyte Recruitment and Activating Cytokines" Interleukins: Molec. Biol. Immunol., ed. Kistimoto, Karger, Basel, vol. 51pp. 236-265 (1992).

McCain, et al., "Leukotriene $B_4$ Stimulates Human Polymorphonuclear Leukocytes to Synthesize and Release Interleukin-8 In Vitro" Am. J. Respir. Cell Molec. Biol., vol. 10, pp. 651-657 (1994).

McCain, et al., "Granulocyte/Macrophage Colony-Stimulating Factor Stimulates Human Polymorphonuclear Leukocytes to Produce Interleukin-8 In Vitro" Am. J. Respir. Cell Molec. Biol., vol. 8, pp. 28-34 (1993).

McIntyre, et al., "Leukotrienes $C_4$ and $D_4$ Stimulate Human Endothelial Cells to Synthesize Platelet-Activating Factor and Bind Neutrophils" Proc. Natl. Acad. Sci. USA, vol. 83, pp. 2204-2208 (1986).

Miller et al., "Vaccination of Rhesus Monkeys with Synthetic Peptide in a Fusogenic Proteoliposome Elicits Simian Immunodeficiency Virus-Specific CD8[+] Cytotoxic T Lymphocytes" J. Exp. Med., vol. 176, pp. 1739-1744 (1992).

Miller, et al., "Bio9logy and Biochemistry of the Chemokines: A Family of Chemotactic and Inflammatory Cytokines" Crit. Rev. Immunol., vol. 12, Nos. 1-2, pp. 17-46 (1992).

Nakamura, et al., "Purification and Properties of Bacteroides Heparinolyticus Heparinase (Heparin Lyase, EC 4.2.2.7)" J. Clin. Microbiol. vol. 26, No. 5, pp. 1070-1071 (1988).

Norgard-Sumnicht et al., "Calcium-Dependent Heparin-Like Ligands for L-Selectin in Nonlymphoid Endothelial Cells" Science, vol. 261, pp. 480-483 (1993).

Oppenheimer-Marks, et al., "Human T Lymphocyte Adhesion to Endothelial Cells and Transendothelial Migration" J. Immunol., vol. 145, No. 1, pp. 140-148 (1990).

Porat, et al., "Interleukin-1 (IL-1) Receptor Blockade Reduces Endotoxin and Borrelia Burgdorferi-Stimulated IL-8 Synthesis in Human Mononuclear Cells" FASEB J., vol. 6, pp. 2482-2486 (1992)

Rot, "Endothelial Cell Binding of NAP-1/IL-8: Role in Neutrophil Emigration" Immunol. Today, vol. 13, No. 8m pp. 291-294 (1992).

Samuelsson, et al., "Leukotrienes and Lipoxins: Structures, Biosynthesis, and Biological Effects" Science, vol. 237, pp. 1171-1176 (1987).

Sasisekharan, et al., "Cloning and Expression of Heparinase I Gene From Flavobacterium Heparinum" Proc. Natl. Acad. Sci. USA, vol. 90, pp. 3660-3664 (1993).

Sawyer, et al., Polymorphonuclear Neutrophils: An Effective Antimicrobial Force Rev. Infect. Dis., vol. 11, Suppl. 7, pp. S1532-1544 (1989).

Saylers, et al., "Fermentation of Mucin and Plant Polysaccharides by Strains of Bacteroids from the Human Colon" Appl. Environ. Microbiol., vol. 33, No. 2, pp. 319-322 (1977).

Smith, et al., "Chemotactic Factors Regulate Lectin Adhesion Molecule 1 (LECAM-1)-Dependent Neutrophil Adhesion to Cytokine-Stimulated Endothelial Cells In Vitro" Clin. Invest., vol. 87, pp. 609-618 (1991).

Springer, "Adhesion Receptors of the Immune System" Nature, vol. 346, pp. 425-434 (1990).

Strieter, et al., "Endothelial Cell Gene Expression of a Neutrophil Chemotactic Factor by TNF-$\alpha$, LPS, and IL-1$\beta$" Science, vol. 243, pp. 1467-1469 (1989).

Sugama et al., "Thrombin-Induced Expression of Endothelial P-Selectin and Intercullular Adhesion Molecule-1: A Mechanism for Stabilizing Neutrophil Adhesion" J. Cell Biol., vol. 119, No. 4, pp. 935-944 (1992).

Tanaka, et al., "T-Cell Adhesion Induced by Proteoglycan-Immobilized Cytokine MIP-1$\beta$" Nature, vol. 361, pp. 79-82 (1993).

Taub, et al., "Preferential Migration of Activated CD4[+] and CD8[+] T Cells in Response to MIP-1$\alpha$ and MIP-1$\beta$" Science, vol. 260, pp. 355-358 (1993).

Webb et al., "Binding to Heparan Sulfate or Heparin enhances Neutrophil Responses to Interleukin 8" Proc. Natl. Acad. Sci. USA, vol. 90, pp. 7158-7162 (1993).

Winn et al., "CD18-Independent Neutrophil and Mononuclear Leukocyte Emigration Into the Peritoneum of Rabbits" J. Clin. Invest., vol. 92, pp. 1168-1173(1993).

Witt et al., "Differential Binding of Chemokines to Glycosaminoglycan Subpopulations" Curr. Biol., vol. 4, No. 5, pp. 394-400 (1994).

Yoshida, et al., 10th Annual Symposium of Glycoconjugates, Jerusalem (1989).

Zimmerman, et al., "Endothelial Cell-Associated Platelet-Activating Factor: A Novel Mechanism for Signaling Intercellular Adhesion" J. Cell Biol. vol. 110, pp. 529-540 (1990).

Zimmerman et al., "Leukocyte-Endothelial Cell Interactions" Immunol. Today, vol. 13 (1992).

Zucker, et al., "Immunoregulatory Activity of Peptides Related to Platelet Factor 4" Proc. Natl. Acad. Sci. USA, vol. 86, pp. 7571-7574 (1989).

Gilat et al., "Regulation of Adhesion of CD4 + T Lymphocyes to Intact or Heparinase-Treated Subendothelial Extracellular Matrix by Diffusible or Anchored RANTES and MIP-1B," *J. Immun.*, 153(11):4899-4906 (1994).

Haber, "Engineered Antibodies as Pharmacological Tools," *Immun. Rev.*, 130:189-212 (1992).

Luster et al., "The IP-10 Chemoklne Binds to a Specific Cell Surface Heparan Sulfate Site Shared with Platelet Factor 4 and Inhibits Endothelial Cell Proliferation," *J. Exp. Med.*, 182:219-231 (1995).

Nelson et al., "Heparin Oligosaccharides Bind L- and P- Selection and Inhibit Acute Inflammation," *Blood*, 82(11):3253-3258 (1993).

International Search Report for International Application No. PCT/US96/15593, dated Jan. 21, 1997.

* cited by examiner

USE OF HEPARINASES TO DECREASE INFLAMMATORY RESPONSE

This application is a continuation of U.S. application Ser. No. 11/118,477 filed May 2, 2005, abandoned which is a continuation of U.S. application Ser. No. 08/722,659 filed Sep. 27, 1996, abandoned, which claims priority to U.S. Provisional Application No. 60/004,622, filed 29 Sep. 1995, which are expressly incorporated herein by reference.

FIELD OF THE INVENTION

This invention is in the field of medical treatments and is directed to the use of heparinase enzyme as a treatment or prophylactic for reducing localized inflammatory responses.

BACKGROUND OF THE INVENTION

An inflammatory response is local response to cellular injury that is marked by capillary dilation, leukocytic infiltration, redness, heat, and pain and serves as a mechanism initiating the elimination of noxious agents and of damaged tissue.

A generalized inflammatory response within a tissue occurs by the recruitment of leukocytes to the tissue. Destruction of bacteria, foreign materials and/or damaged cells occurs through phagocytosis and/or extracellular degranulation (secretion of degradative enzymes, antimicrobial proteins and myeloperoxidase, which forms superoxides from secreted $H_2O_2$). While most localized inflammatory responses are beneficial, harmful inflammatory responses can occur. Many harmful inflammatory responses also involve accumulation of leukocytes within a tissue. This accumulation results in the destruction of viable cells and tissue. In addition to damaging tissue, these responses are detrimental to, or debilitating for, the afflicted individual. Examples of detrimental inflammatory responses can include the following; ischemia/reperfusion injury following myocardial infarction, shock, stroke, organ transplantation, cardiopulmonary bypass surgery, allograft rejection, rheumatoid arthritis, antigen-induced asthma, allergic rhinitis, and glomerulonephritis (see the review in; Harlan, et al., *Immunol. Rev.*, 114:5-12, 1990; Carlos and Harlan, *Blood*, 84:2068-2101, 1994.)

Leukocyte recruitment involves a cascade of cellular events, beginning with activation of vascular endothelium by damaged or infected tissue adjacent to the endothelium. Activation of the endothelium results in enhanced adhesion of leukocytes to the endothelial cells, and transendothelial migration (extravasation) by bound leukocytes into the damaged tissue. Endothelial activation is manifested by a short-term, rapid, and/or a long-term stimulation of the endothelial cells.

Activators such as thrombin, chemoattractant leukotrienes, $B_4$, $C_4$ and $D_4$ ($LTB_4$, $LTC_4$ & $LTD_4$), and histamine cause rapid, transient (<30 minutes) endothelial cell activation, independent of protein synthesis, and can increase endothelial cell surface levels of the chemoattractants such as platelet activating factor (PAF; a glycerophospholipid) and $LTB_4$ (shown for histamine), and adhesion molecules; ICAM-1 (shown for thrombin) and P-selectin (Zimmerman, et al., *J. Cell Biol.*, 110:529-540, 1990; Sugama, et al., *J. Cell Biol.*, 119:935-944, 1992; McIntyre, et al. *Proc. Natl. Acad. Sci. USA*, 83:2204-2208, 1986; Lorant, et al., *J. Cell Biol.*, 115:223-234, 1991). The outcome of rapid activation of endothelial cells is increased leukocyte adhesion to the endothelium (Hoover, et al., *Proc. Natl. Acad. Sci. USA*, 81:2191-2194, 1984; Zimmerman, et al., *J. Cell Biol.*, 110:529-540, 1990; Hanahan, et al. *Ann. Rev. Biochem.*, 55:483-509, 1986). However, increased $LTB_4$ surface levels have not been shown to directly increase transendothelial migration of neutrophils (Hughes, et al., *Prost. Leuk. Essent. F. A.*, 45:113-119, 1992), and in certain situations, PAF is not necessary for adhesion of leukocytes to activated endothelium (Kuijpers, et al., *J. Cell Biol.*, 117:565-574, 1992).

Long-term (hours in duration) protein synthesis dependent, endothelial cells activation is produced by cytokines, such as IL-1b and TNF-a, and by lipopolysaccharide (LPS) and results in maintenance of increased surface levels of adhesion molecules: E-selectin, P-selectin, ICAM-1 and VCAM-1 (reviewed by Carlos, and Harlan, *Blood*, 84:2068-2101, 1994). IL-1b and TNF-a also increase the synthesis of PAF by endothelial cells (Kuijpers, et al., *J. Cell Biol.*, 117:565-574, 1992). In addition, endothelial cell activation by IL-1b, TNF-a, LPS and histamine has been shown to increase the synthesis and secretion of the chemokine, IL-8 (Strieter, et al., *Science*, 243:1467-1469, 1989; Jeannin, et al., *Blood*, 84:2229-2233, 1994).

Chemokines, IL-8 and MCP-1, have been shown to be produced by and to be present on the endothelial cells surface (Huber, et al., *Science*, 254:99-102, 1991; Springer, *Nature*, 346:425-434, 1990). The chemokine, MIP-1b, has been shown to be present on lymph node endothelium, in vivo (Taub, et al., *Science*, 260:355-359, 1993; Tanaka, et al., *Nature*, 361:79-82, 1993). The chemokines; RANTES, MIP-a, MIP-b, MCP-1 and IL-8 are all heparin binding proteins, which after being secreted, bind to cell surface and extracellular matrix proteoglycans possessing heparin and heparan sulfate moieties (reviewed by Miller, et al., *Crit. Rev. Immunol.*, 12:17-46, 1992).

Heparin and heparan sulfate are similar glycosaminoglycan moieties found interspersed on the same unbranched carbohydrate chains. They are covalently attached to the protein backbones of proteoglycans. Despite what these two names imply, heparin is more highly sulfated than is heparan sulfate. Proteoglycans are present on cell surfaces and in extracellular matrices (e.g. in the basement membrane of endothelium). Because of difficulty in distinguishing regions of heparin and heparan sulfate on the same carbohydrate chain, little data exists on the binding preference of chemokines for either heparin or heparan sulfate moieties. There is some indication that chemokines IL-8 and GRO bind with greater affinity to heparan sulfate than heparin, and that PF4 and NAP-2 bind with greater affinity to heparin moieties (Witt, and Lander, *Curr. Biol.*, 4:394400, 1994). Generally, chemokines are referred to as heparin binding proteins. C-terminal regions of the chemokines IL-8, PF4, MCP-1 and NAP-2 have been shown to form an a-helix, and to bind to heparin/heparan sulfate (Webb, et al., *Proc. Natl. Acad. Sci. USA*, 90:7158-7162, 1993; Zucker, et al., *Proc. Natl. Acad. Sci. USA*, 86:7571-7574, 1989; Matsushima, et al., in *Interleukins: Molec. Biol. Immunol.*, ed. Kistimoto, Karger, Basel, 236-265, 1992). This is likely to be a structure, common to all of the chemokines.

All of the molecules mentioned above, which are expressed by activated endothelial cells (PAF, $LTB_4$, selectins, CAMs and chemokines), are present on the endothelial cell surface, and are localized to vascular endothelium adjacent to sites of damaged tissue. Blood-borne leukocytes which interact with these molecules will also be localized in their binding in the area of the damaged tissue. The outcome of long-term activation of endothelium is increased adhesion and extravasation of leukocytes and a significant localized accumulation of leukocytes in adjacent tissue, which cannot occur during short-term activation (Ebisawa, et al., *J. Immunol.*, 149:4021-4028, 1992; Huber, and Weiss, *J. Clin. Invest.*, 83:1122-1129, 1989; Oppenheimer-Marks, et al., *J. Immunol.*, 145:140-148, 1990).

Adhesion of leukocytes to endothelium is thought to be a two step process (reviewed by Carlos, and Harlan, *Blood*, 84:2068-2101, 1994). Initially, leukocytes roll along the surface of blood vessels. Increased rolling is initially mediated on vascular endothelium (within the first 30 minutes) by interactions between Sialyl Lewisx structures on the leukocyte surface and P-selectin and E-selectin, which are increased on activated endothelial cells (Ley, et al., *Blood*, 85:3727-3735, 1995). Increased rolling is also mediated (after 40 minutes) by interactions between L-selectin on leukocyte cellular membranes and heparin-like molecules on the vascular endothelium, which are cytokine-inducable (Karin. et al., *Science*, 261:480-483, 1993), or between L-selectin on lymphocytes and vascular addressins; Gly-CAM-1, CD34 and MAdCAM-1 on high endothelial venules (HEVS) in lymphoid tissue. The second step, firm adhesion of leukocytes to endothelial cells, is based on interactions between leukocyte integrins (e.g. LFA-1, Mac-1, VLA-4) and endothelial cellular adhesion molecules (CAMs; e.g. ICAM-1, ICAM-2, VCAM-1, MAdCAM-1). Leukocytes flatten on the endothelial surface, and shed L-selectin, concomitant with firm adhesion (Kishimoto, et al., *Science*, 245:1238-1242, 1989; Jutila, et al., *J. Immunol.*, 143:3318-3324, 1989; Smith, et al., *Clin. Invest.*, 87:609-618, 1991).

Selectin and CAM levels increase on the endothelium surface in response to many cytokines and chemoattractants. These increases are dependent on synthesis and/or secretion of additional selectin and CAM molecules onto the cell surface. In contrast, activation of leukocytes for firm adhesion has been shown to occur within second (Bargatze, et al., *J. Exp. Med.*, 178:367-373, 1993), through increased secretion of integrins, and more importantly, through induction of conformational changes in cell surface integrins (integrin activation), which permits tight binding of the integrins to CAMs (reviewed in Zimmerman, *Immunol. Today*, 13:93-99, 1992).

PAF and E-selectin can activate integrins for endothelial cell adhesion (Lorant et al., *J. Biol. Chem.*, 115:223-234, 1991; Lo, *J. Exp. Med.*, 173:1493-1500, 1991). The presence of MIP-1b, immobilized by binding to CD44 (possesses heparin/heparan sulfate moieties), or a heparin-BSA conjugate, has been shown to be required for CD8+ T-cell binding to immobilized VCAM-1 molecules. This binding was shown to be blocked by an antibody to VLA-4, indicating that MIP-1b activates VLA-4 on the T-cell surface (Tanaka, et al., *Nature*, 361:79-82, 1993). An increase in the level of integrin, CD18 (part of Mac-1), on the surface of neutrophils has been shown to occur when neutrophils contact endothelium, which has been stimulated with IL-1b. An antibody to IL-8 inhibited the CD18 up-regulation, and also inhibited neutrophil adhesion (Huber, *Science*, 254:99-102, 1991). Thus, chemokines can act as direct activators of leukocyte adhesion. In contrast, Luscinaskas et al. (*J. Immunol.*, 149: 2163-2171, 1992) has demonstrated that pretreatment of neutrophils with IL-8 inhibits neutrophil attachment, and addition of exogenous IL-8 detached neutrophils adhering to activated endothelial cells. Rot (*Immunol. Today*, 13:291-294, 1992) has reconciled these contradictory results by proposing that IL-8 bound to the endothelial cells surface promotes adhesion, while soluble IL-8 can inhibit it.

Different chemokines activate different leukocytes. IL-8 activates neutrophils, eosinophils and T cells. RANTES activates monocytes, eosinophils and T cells. MCP-1 activates monocytes. MIP-1a activates CD4+ T cells, monocytes and B cells, while MIP-1b activates monocytes and CD8+ T cells (reviewed in Lasky, *Current Biol.*, 3:366-378, 1993). Different combinations of selectins, integrins, CAMs and chemokines are thought to select for the adhesion and migration of the leukocyte subtypes observed in different inflamed tissues (Butcher, *Cell*, 67:1033-1039, 1991).

The importance of interactions of integrins, CD11/CD18 (Mac-1), and ICAMs in adhesion and extravasation of leukocytes has been demonstrated in numerous systems by the use of antibodies to these molecules. The antibodies interfere with the function of the adhesion molecules and block or reduce leukocyte recruitment. The leukocyte adhesion deficiency (LAD) Type I syndrome results in a partial or total absence of the integrin, CD18, on the leukocytes of affected patients. Neutrophil recruitment to sites of inflammation is negligible. However, monocyte and eosinophil recruitment is normal, indicating that an alternative set of adhesion molecules may function for recruitment of these cells, perhaps VLA-4 and VCAM-1 (Harlan, *Clin. Immunol. Immunopath.*, 67:S16-S24, 1993). VLA-4 is not expressed by neutrophils (Winn and Harlan, *J. Clin. Invest.*, 92:1168-1174, 1993). As mentioned previously, chemokines are important for activation and increased surface levels of integrins VLA-4 and CD18 on leukocytes. IL-8 immobilized on a polycarbonate filter has been shown to be adequate for directing migration of neutrophils through the filter (Rot, *Immunol. Today*, 13:291-294). Huber, et al. (*Science*, 254: 99-102, 1991) has shown that a transendothelial gradient of bound IL-8, produced by IL-1b stimulated endothelial cell monolayers, is necessary for extravasation of neutrophils. These neutrophils were pre-activated with IL-8 and did bind to the endothelial cells, but did not migrate until the IL-8 gradient was present. This gradient extended from the endothelial cells luminal surface through the basement membrane underlying the endothelial cell monolayer. Washing bound IL-8 from the basement membrane underlying activated endothelial cells prevented migration across the monolayer. In addition, an antibody to IL-8 inhibited 70-80% of the neutrophil migration. Kuijpers et al. (*J. Cell Biol.*, 117:565-572, 1992) used an anti-IL-8 antibody to produce a 60% reduction in neutrophil migration across IL-1b and TNF-a activated endothelium, and addition of a PAF receptor antagonist produced an 85-90% reduction in migration. These results are in contrast to experiments which showed that IL-8 pretreated neutrophils were inhibited in their ability to migrate through an activated endothelial cell monolayer (Luscinaskas et al., *J. Immunol.*, 149:2163-2171, 1992). Thus, it is likely that chemokines not only activate leukocytes for adhesion, but that a bound gradient of chemokine is important in extravasation of leukocytes. The presence of soluble chemokine can interfere with adhesion and migration along bound chemokine gradient. A discussed below, in vivo localized concentration increases in soluble chemokines would be minimized by blood flow.

Once activated leukocytes have begun to accumulate within a damaged tissue, they can augment the accumulation of additional leukocytes, by synthesis and secretion of cytokines, chemokines, and $LTB_4$. LPS has been shown to directly increase monocyte IL-1b expression (Porat, et al., *FASEB J.*, 6:2482-2489, 1992). IL-8, IL-1b and TNF-a are produced by neutrophils activated with GM-CSF, another cytokine produced by activated macrophages, endothelium and T-cells (McCain, et al., *Am. J. Respir. Cell Molec. Biol.*, 8:28-34, 1993; Lindemann, et al., *J. Immunol.* 140:837-839, 1988; Lindemann, et al., *J. Clin. Invest.*, 83:1308-1312, 1989). IL-1b and TNF-a have been shown to stimulate monocytes, thereby increasing the expression of the chemokines, IL-8 and MIP-1a (Lukacs, et al., *Blood,* 82:3668-3674, 1993). Activated neutrophils and monocytes have been shown to be a major source of LTB$_4$ production (Samuelsson, et al., *Science,* 237:1171-1176, 1987; Brach, et al., *Eur. J. Immunol.*, 22:2705-2711, 1992). As discussed previously, LTB$_4$ is not directly involved in further recruitment of leukocytes, but because neutrophils stimulated with LTB$_4$ produce IL-8, the LTB$_4$-stimulated neutrophils could promote further neutrophil recruitment, indirectly, through formation of an IL-8 gradient (McCain, et al., *Am. J. Respir. Cell Molec. Biol.*, 10:651-657, 1994). The continued recruitment of leukocytes by these leukocyte-derived activators would require using the vascular endothelium as an intermediate. Endothelial cells and basement membranes would bind and display neutrophil-derived chemokines, forming a gradient, or leukocyte-derived cytokines would activate the endothelium, which would also cause the creation of a chemokine gradient.

Blood flow in the vasculature would prevent a localized concentration increase in soluble activation factors (cytokines, chemokines and chemoattractants), produced by a tissue-localized inflammatory response. If a local inflammation is producing high blood concentrations of activators, a systemic activation of leukocytes could occur (Finn, et al., *J. Thorac. J. Surg.*, 105:234-241, 1993). The activated leukocytes would then bind transiently to unactivated endothelium and/or degranulate, causing sepsis (Sawyer, et al., *Rev. Infect. Dis.*, 11:S1532-1544, 1989). In situations where some blood-borne leukocytes are activated by a localized inflammation (not all of the activated leukocytes extravasate), the activated leukocytes would produce and secrete additional cytokines, chemokines, and LTB$_4$ into the blood. This increase in activator concentration could up-regulate unactivated cells and amplify the systemic response.

Although the mechanism of inflammatory responses has been given in some detail, there is still a need for an effective treatment and pharmaceutical compositions for reducing or preventing localized inflammatory responses.

SUMMARY OF INVENTION

This invention is directed to the discovery that heparinase degrading enzymes, either separately or in combination, can be used to decrease localized inflammatory response. The heparinases useful in this invention can be from a variety of sources: heparinases I, II, and III from the Gram negative bacterium *Flavobacterium heparinum*, heparinase from *Bacteroides* strains, heparinase from *Flavobacterium* Hp206, heparinase from *Cytophagia* species, and heparanases from mammalian cells. These enzymes, either singly or in combination, are referred to herein as heparinase or heparinase enzyme.

Heparin and heparan sulfate moieties are degraded on the surface of endothelial cells and from basement membranes by administration of heparinase. Removal of heparin and heparan sulfate moieties from up-regulated proteoglycans on activated endothelial cells prevents L-selectin, found on leukocytes, from interacting with the proteoglycans. By decreasing L-selectin-proteoglycan interactions, leukocyte rolling on activated endothelium can be inhibited.

In addition, when heparin and heparan sulfate moieties are removed from the surface of activated endothelial cells and from their basement membrane, chemokines, which are bound to the heparin and heparan sulfate, are released from the cell surfaces and basement membrane. The loss of bound chemokines decreases the localized concentration of chemokines and disrupts the chemokine gradient produced by activated endothelium, thereby inhibiting chemokine activation of rolling leukocytes, which is required for firm adhesion, and preventing extravasation of leukocytes along the chemokine gradient. By this invention, decreased leukocyte rolling, activation and extravasation can inhibit localized tissue inflammatory responses by interfering with fundamental mechanisms of leukocyte recruitment.

Heparinase enzyme can be targeted to specific cell types, tissues or organs by the selected method of administration, which deliver localized high concentrations of the enzymes or physically limit the dispersal of the enzymes. Additionally, according to this invention heparinase can be targeted by fusion of the enzymes to binding domains from antibodies, growth factors or adhesion molecules. The fusion proteins are produced by construction and expression of gene fusions in recombinant organisms. As examples, the binding domains can recognize cell surface molecules on activated endothelium (e.g., ICAM-1, VCAM-1, P-selectin, E-selectin), or on endothelial cell subtypes (e.g., GlyCAM-1). Targeted fusion enzymes can increase the number and specificity of indications, while decreasing the amounts of enzyme required for efficacy and possible side-effects resulting from treatments.

BRIEF DESCRIPTIONS OF THE DRAWINGS

FIG. 1 is a graph of the counts of 35S-heparin/heparan sulfate released from the surface of endothelial cells by 1.0 IU/ml of heparinase III, which were separated according to size on a gel filtration column. The diamonds indicate counts released by a 5 minute digest, the squares indicate counts released by a 30 minute digest, and the triangles indicate counts released by a 60 minute digest. Background counts from fractionation of mock digests have been subtracted from the fractions derived from the heparinase III digests.

FIGS. 2A and 2B are graphs of the percent of heparin/heparan sulfate present on the unactivated (2A) and IL-1b activated (2B) human endothelial cell line at the indicated times after treatment with 0.1 IU/ml heparinase I, II or III for 1 hour. 125I-bFGF binding to cell surface heparin was used to determine the amount of heparin/heparan sulfate present. Results for heparinase I, II or III-treated cells are indicated by diamonds, squares or triangles, respectively. The vertical lines indicate the standard error of the means.

FIGS. 3A and 3B are graphs of the percent of heparin/haparan sulfate present on the unactivated (3A) and IL-1b activated (3B) human endothelial cell line at the indicated times after treatment with 1.0 IU/ml heparinase I. 125I-bFGF binding to cell surface heparin was used to determine the amount of heparin/heparan sulfate present. Results for 1, 3 or 5 hour treated cells are indicated by diamonds, squares or triangles, respectively. The vertical lines indicate the standard error of the means.

FIGS. 4A and 4B are graphs of the percent of heparin/heparan sulfate present on the unactivated (4A) and IL-1b activated (4B) human endothelial cell line at the indicated times after treatment with 1.0 IU/ml heparinase III. 125I-bFGF binding to cell surface heparin was used to determine the amount of heparin/heparan sulfate present. Results for 1, 3 or 5 hour treated cells are indicated by diamonds, squares or triangles, respectively. The vertical lines indicate the standard error of the means.

Figure 5:
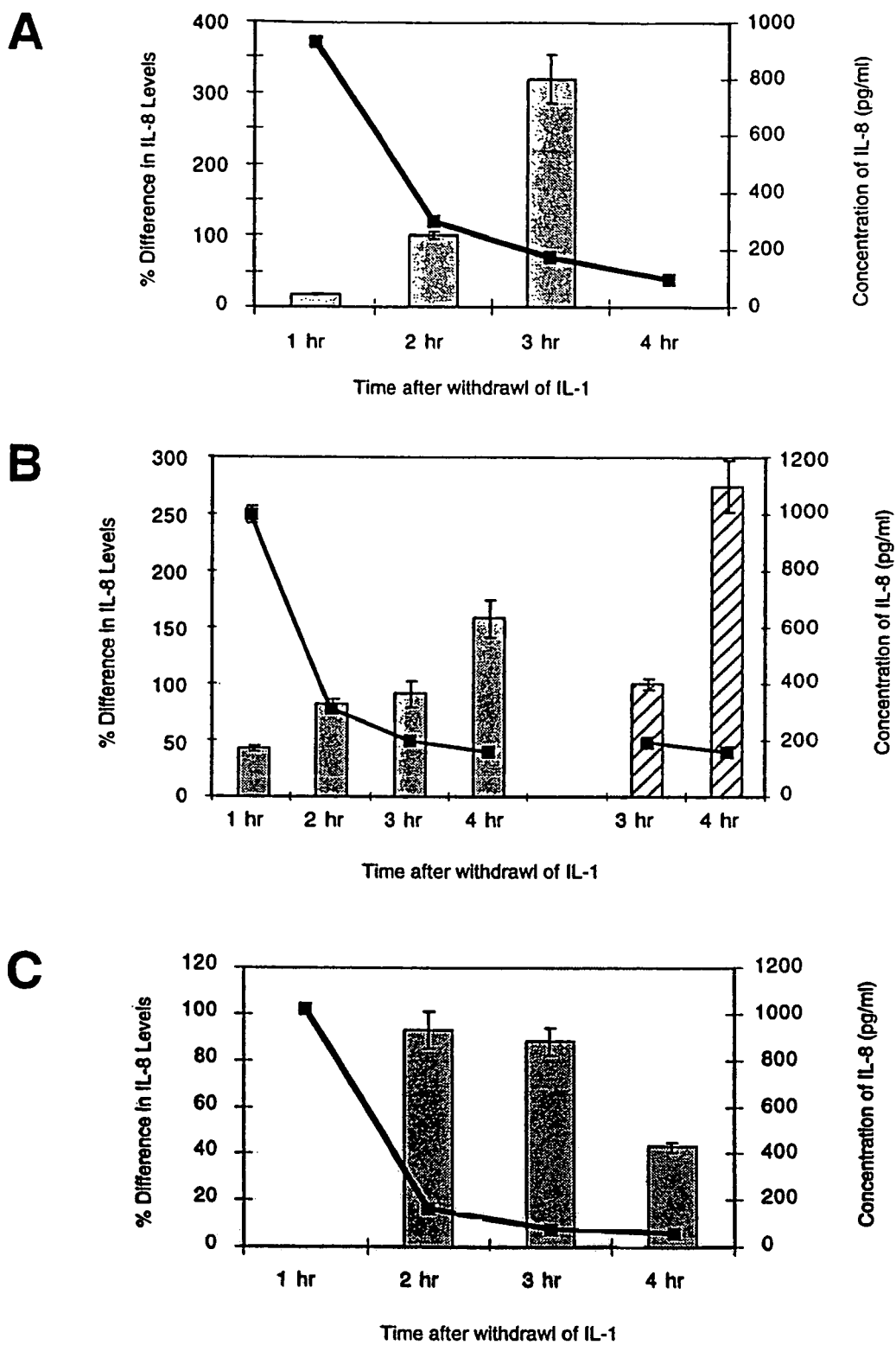

FIG. 5 contains graphs displaying the levels of IL-8 released from IL-1b activated human endothelial cell layers by treatment with 1.0 IU/ml of heparinases; I (5A), II (5B), I+III (bars containing diagonal lines; 5B), and III (5C). The bars represent the percent difference in the concentration of IL-8 found in; supernatants from activated endothelial layers treated with heparinases, versus untreated supernatants from activated endothelial layers (containing only secreted IL-8). Standard errors for these percentage differences are indicated by vertical lines. The lines overlaid on the bars indicate the concentration of IL-8 in the supernatants from the heparinase treated cell layers. The standard errors of these measurements are also indicated by vertical lines (not always visible).

Figure 6:
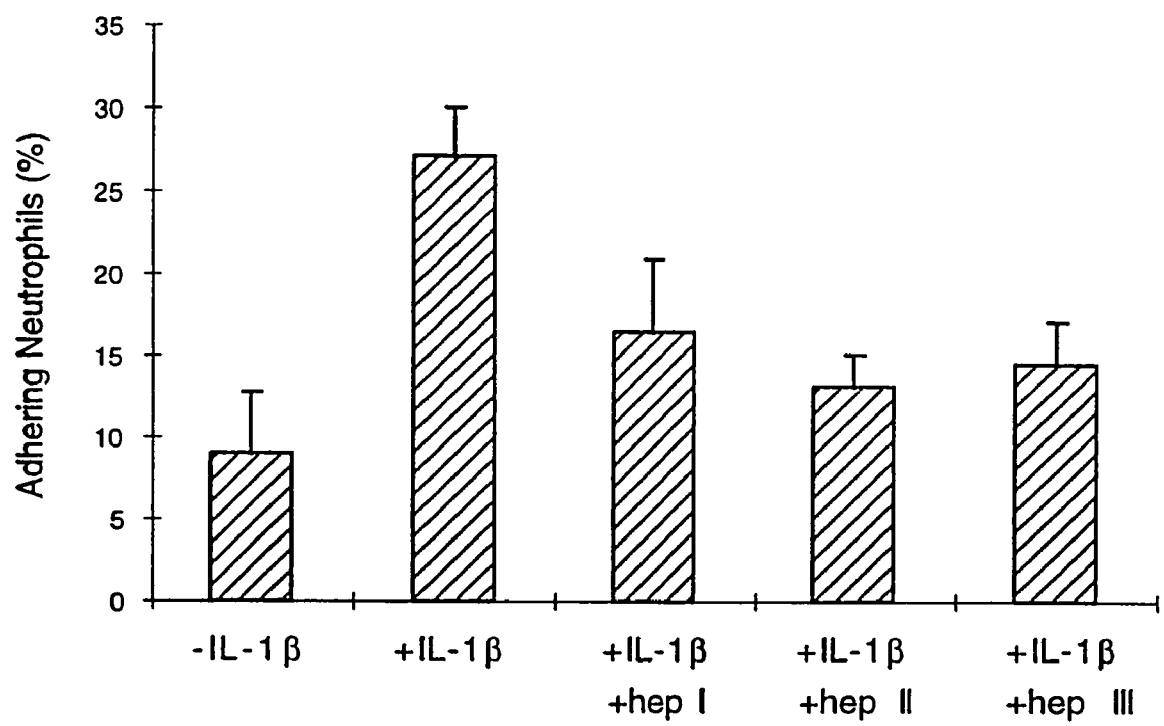

FIG. 6 is a graph of the level of neutrophil adhesion to endothelial cells, which were unactivated, IL-1b activated, or treated with 0.1 IU/ml of heparinases I, II or III after IL-1b activation. The level of adhesion is expressed as the percent of added neutrophils, which are adhering.

FIGS. 7A, 7B and 7C are graphs of the percent inhibition of neutrophil extravasation through IL-1b activated endothelial cell layers, which were treated with heparinases I, II or III, respectively. The bars containing diagonal lines represent results of one hour treatments with 1.0 IU/ml of heparinase. The white bars represent results of one hour treatments with 0.1 IU/ml of heparinase. The black bars represent results of 15 minute treatments with 0.1 IU/ml of heparinase I or III, and the bar containing vertical lines represents results of 15 minute treatments with 1.0 IU/ml of heparinase II. The standard deviations for the percent inhibitions are indicated by vertical lines. The small asterisks indicate results of one hour treatments that were significantly different from the results of the 15 minute treatment with the same heparinase ($P<0.05$). The large asterisks indicate the results of one hour treatments with 1.0 IU/ml of heparinase that were significantly different from the results of one hour treatments with 0.1 IU/ml of the same heparinase. The numbers in parentheses under the bars indicate the number of experiments included in each data set.

Figure 8:
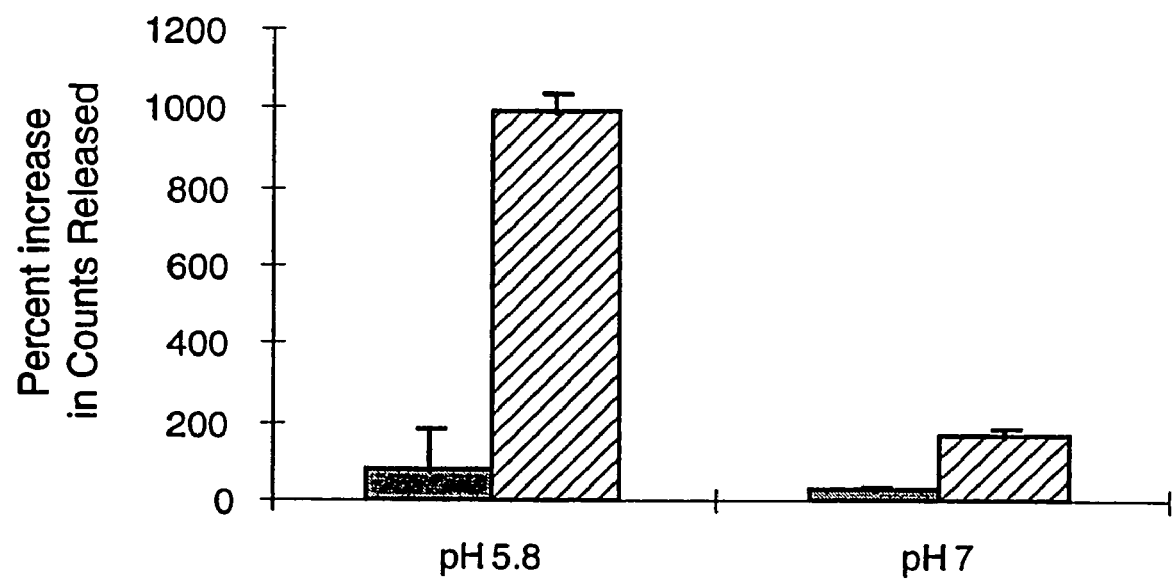

FIG. 8 is a graph showing the activity of human heparinase (b-thromboglobulin) on ECM at pH 5.8 and 7. The solid bars represent the percent difference in $^{35}SO_4$ released from ECM treated with 1 ug of human heparinase versus that released from untreated ECM. The bars containing diagonal lines represent the percent difference in $^{35}SO_4$ released from ECM treated with 5 ug of human heparinase versus that released from untreated ECM. The standard deviation of the means are indicated by vertical lines.

Figure 9:
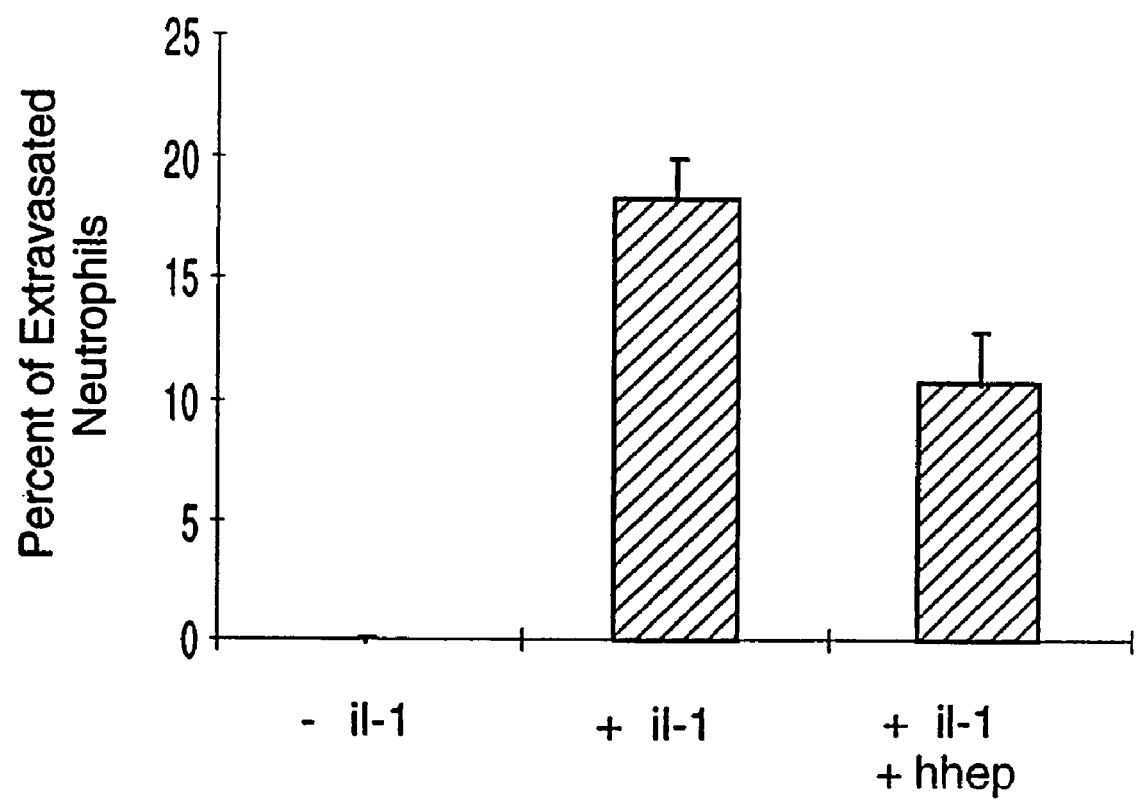

FIG. 9 is a graph which displays the change in the level of neutrophil extravasation upon activation of HUVEC layers with IL-1b, and after treatment of activated HUVEC layers with human heparinase (hhep). The standard deviation of the means are indicated by vertical lines.

Figure 10:
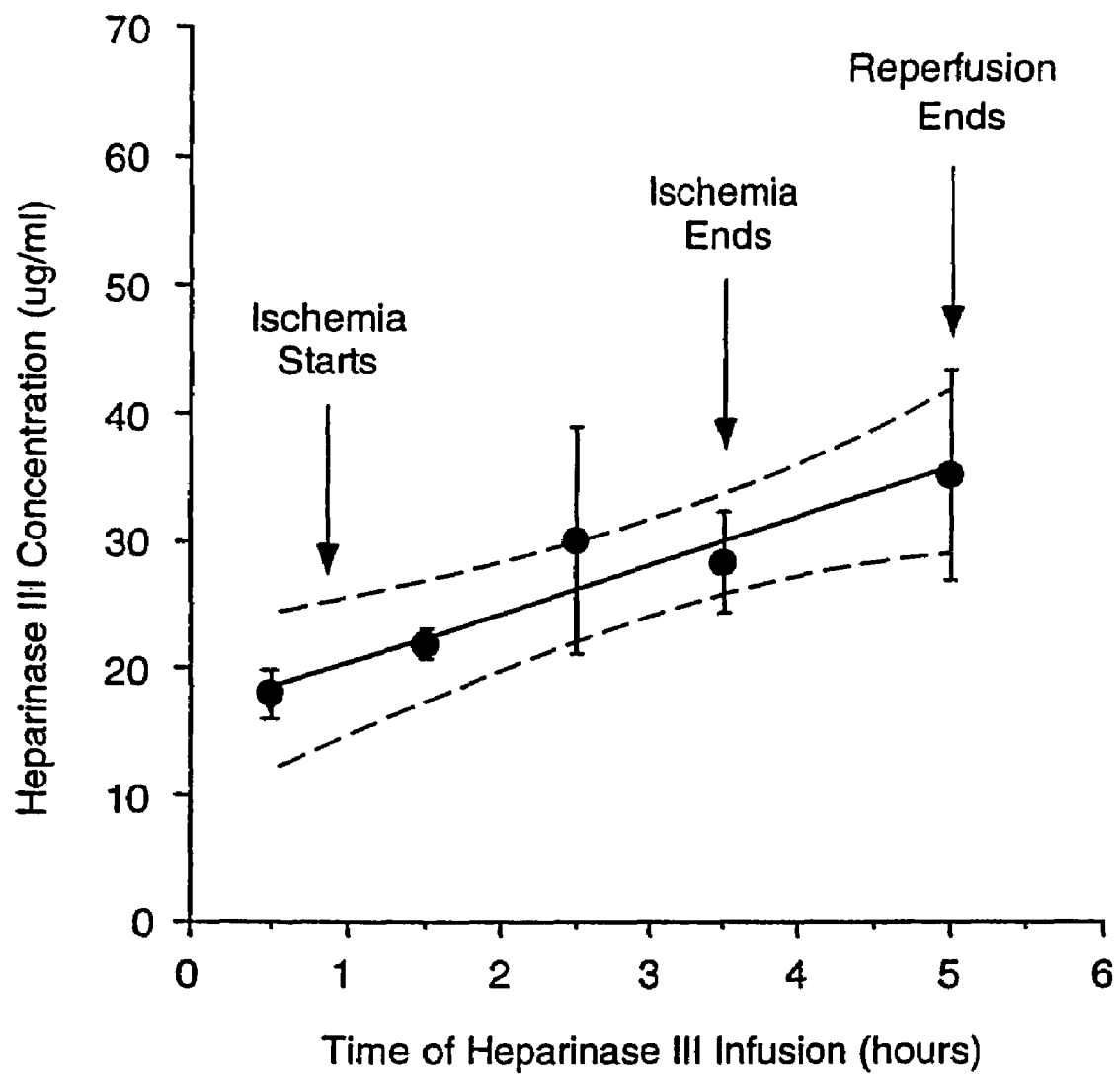

FIG. 10 is a graph of rat plasma heparinase III concentrations over a five hour infusion period. Time points in the protocol are indicated by the arrows, with descriptions above the arrows. The vertical lines indicate the standard error of the means.

Figure 11:
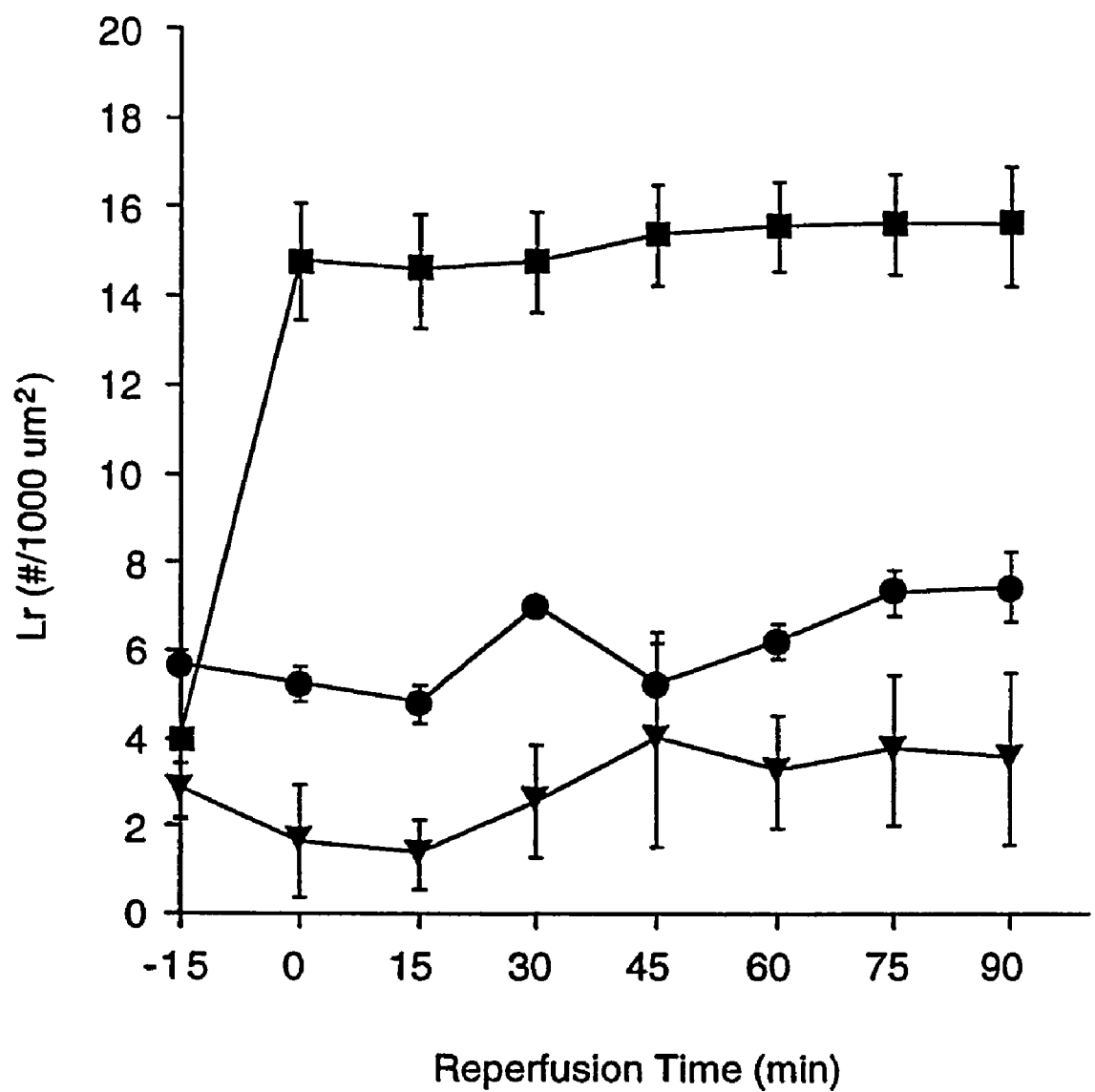

FIG. 11 is a graph of the level of leukocyte rolling in the rat microvasculature after 3 hours of ischemia, during reperfusion. The circles indicate the levels in naive rats, the squares indicate the levels in sham treated rats which underwent ischemia, and the triangles indicate the levels in heparinase treated rats which underwent ischemia. The vertical lines indicate the standard error of the means.

Figure 12:
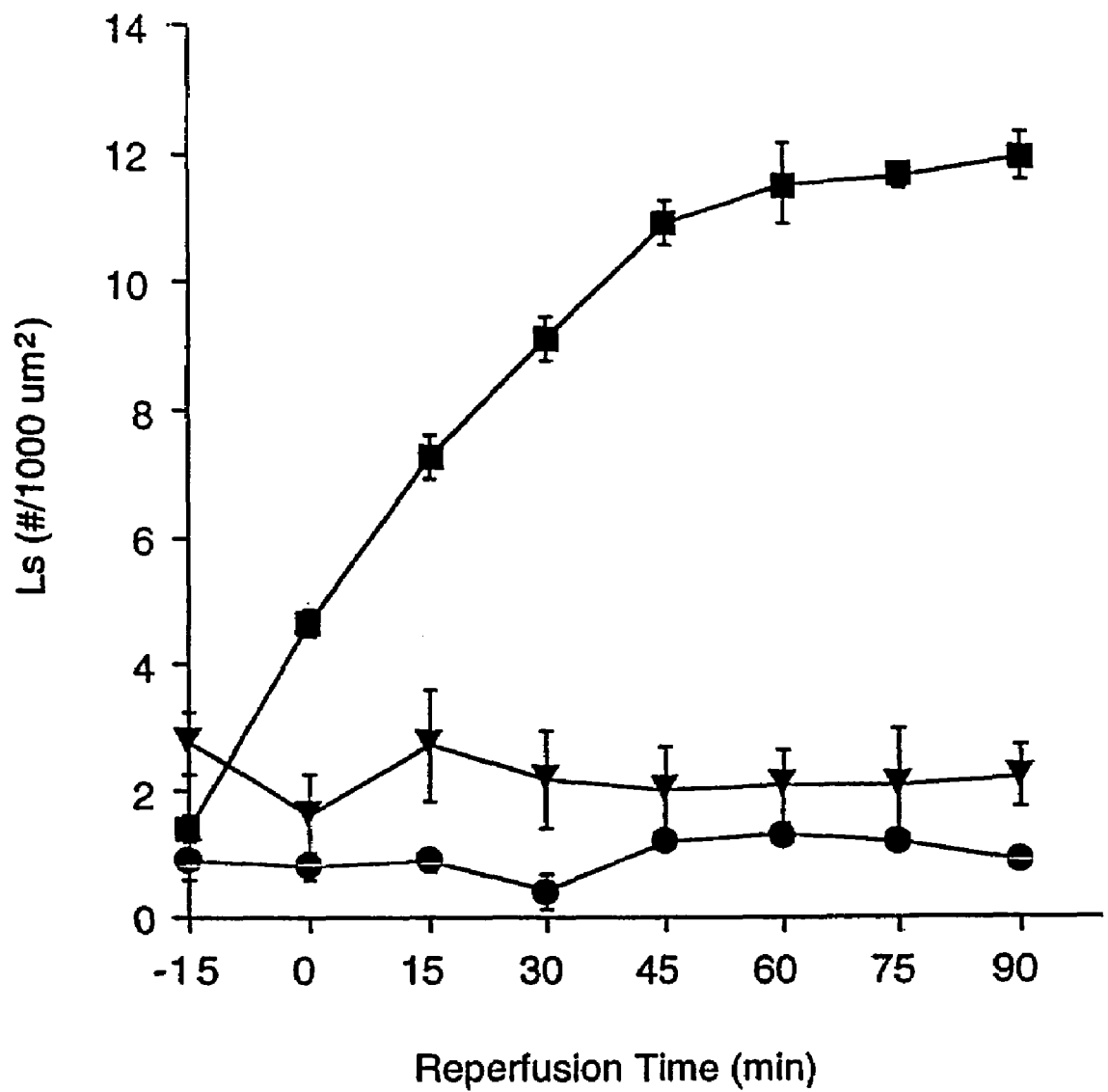

FIG. 12 is a graph of the level of leukocyte adhesion in the rat microvasculature after 3 hours of ischemia, during reperfusion. The circles indicate the levels in naive rats, the squares indicate the levels in sham treated rats which underwent ischemia, and the triangles indicate the levels in heparinase treated rats which underwent ischemia. The vertical lines indicate the standard error of the means.

Figure 13:
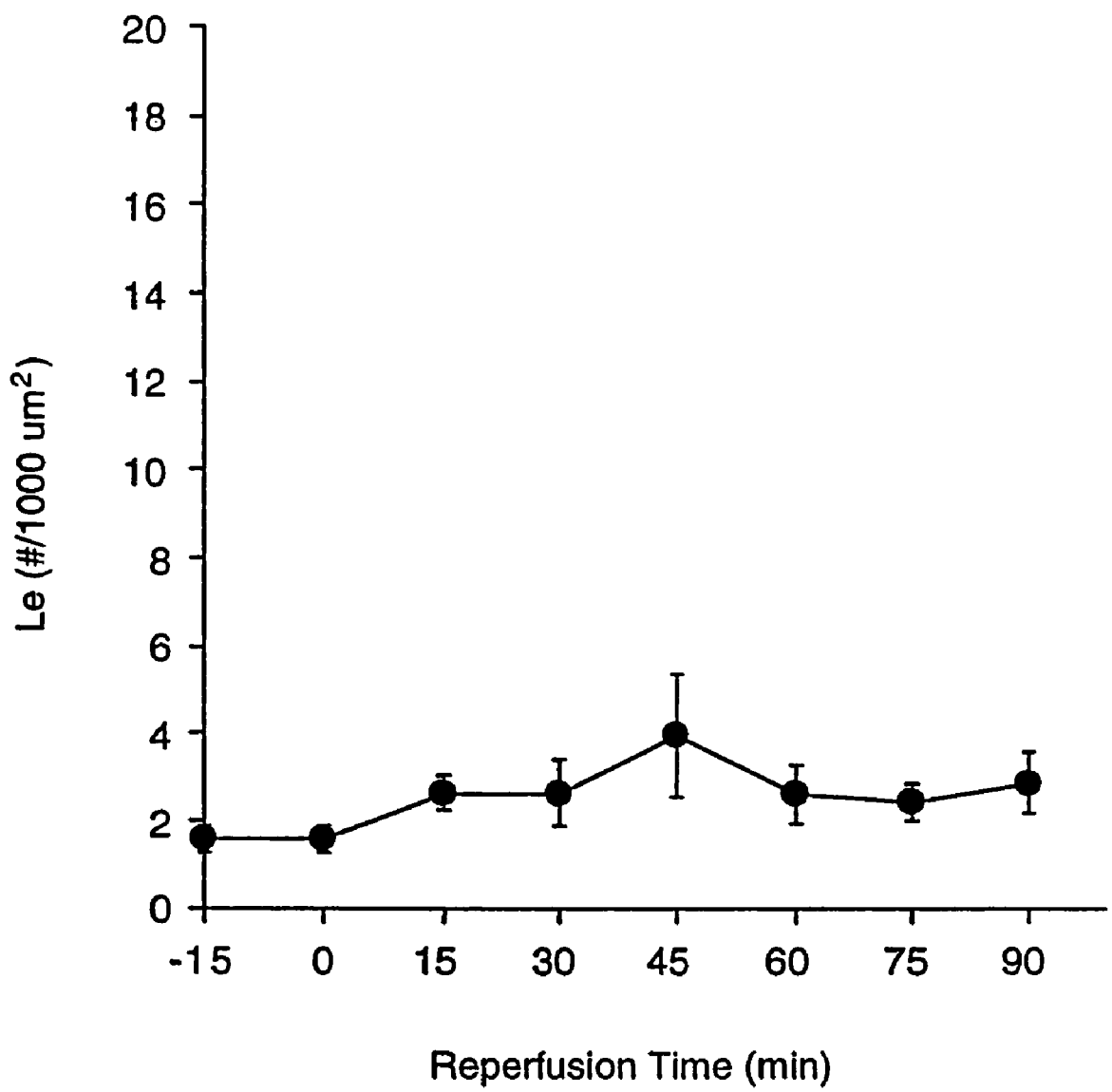

FIG. 13 is a graph of the level of leukocyte extravasation in the rat microvasculature after 3 hours of ischemia, during reperfusion. The circles indicate the levels in heparinase treated rats which underwent ischemia. The vertical lines indicate the standard error of the means.

Figure 14:
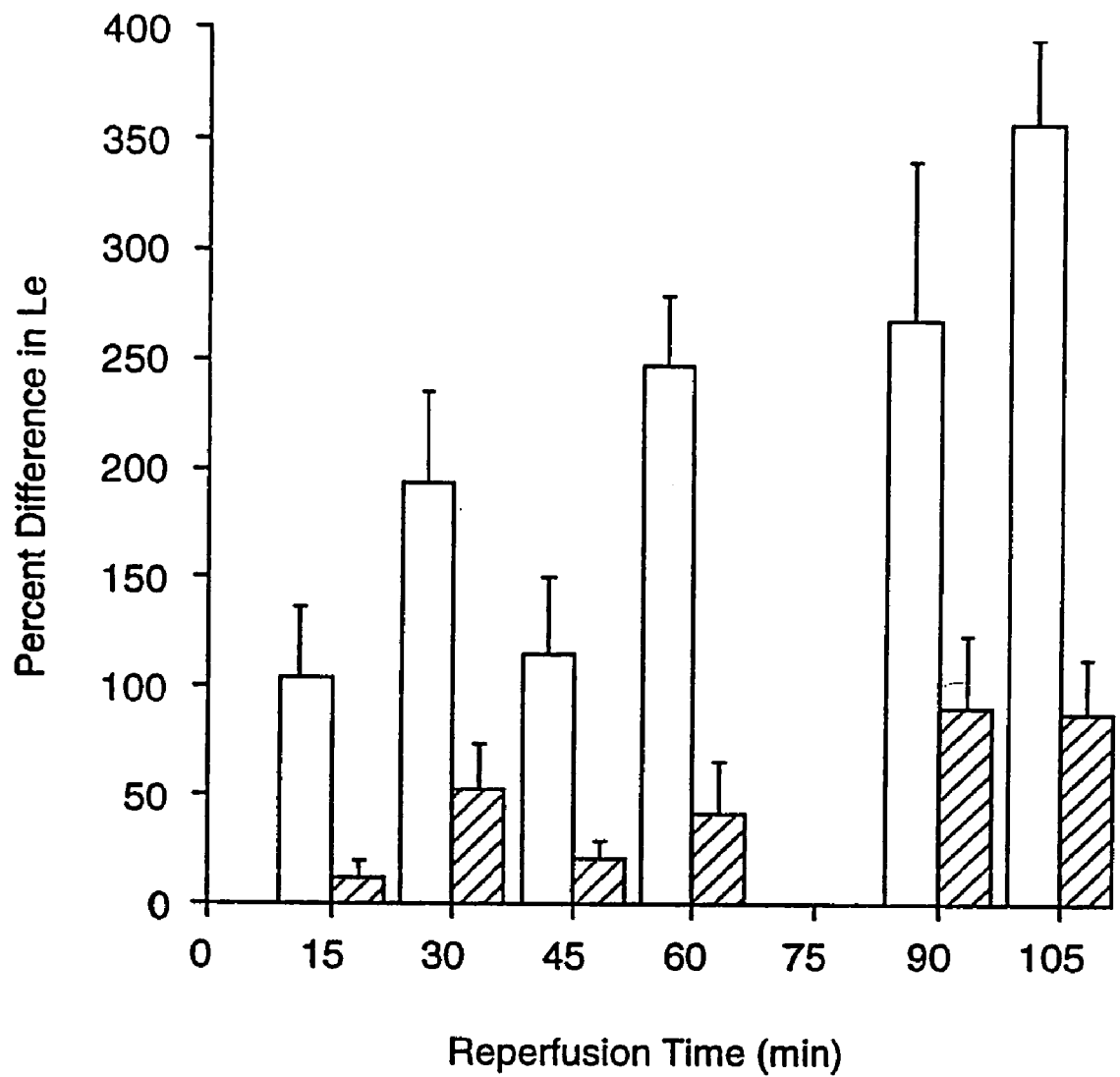

FIG. 14 is a graph of the level of leukocyte extravasation in the rat microvasculature after 2 hours of ischemia, during reperfusion. The open bars are the percent difference in the levels in sham treated rats versus the levels in naive rats. The bars containing diagonal lines are the percent difference in the levels in heparinase treated rats versus the levels in naive rats. The vertical lines indicate the standard error of the means.

Figure 15:
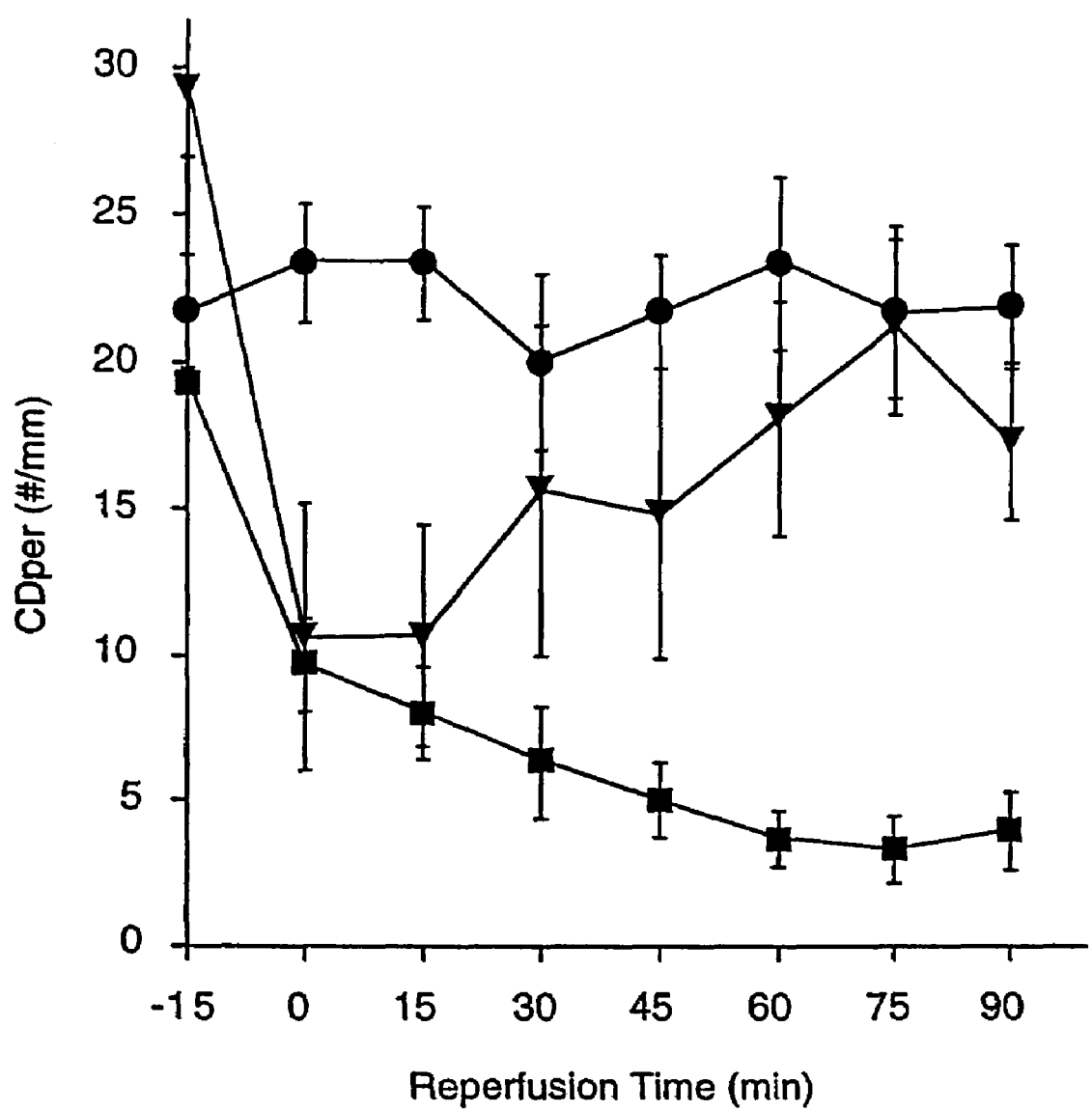

FIG. 15 is a graph of the level of perfusion in rat postcapillary venules after 3 hours of ischemia, during reperfusion. The circles indicate the levels in naive rats, the squares indicate the levels in sham treated rats which underwent ischemia, and the triangles indicate the levels in heparinase treated rats which underwent ischemia. The vertical lines indicate the standard error of the means.

Figure 16:
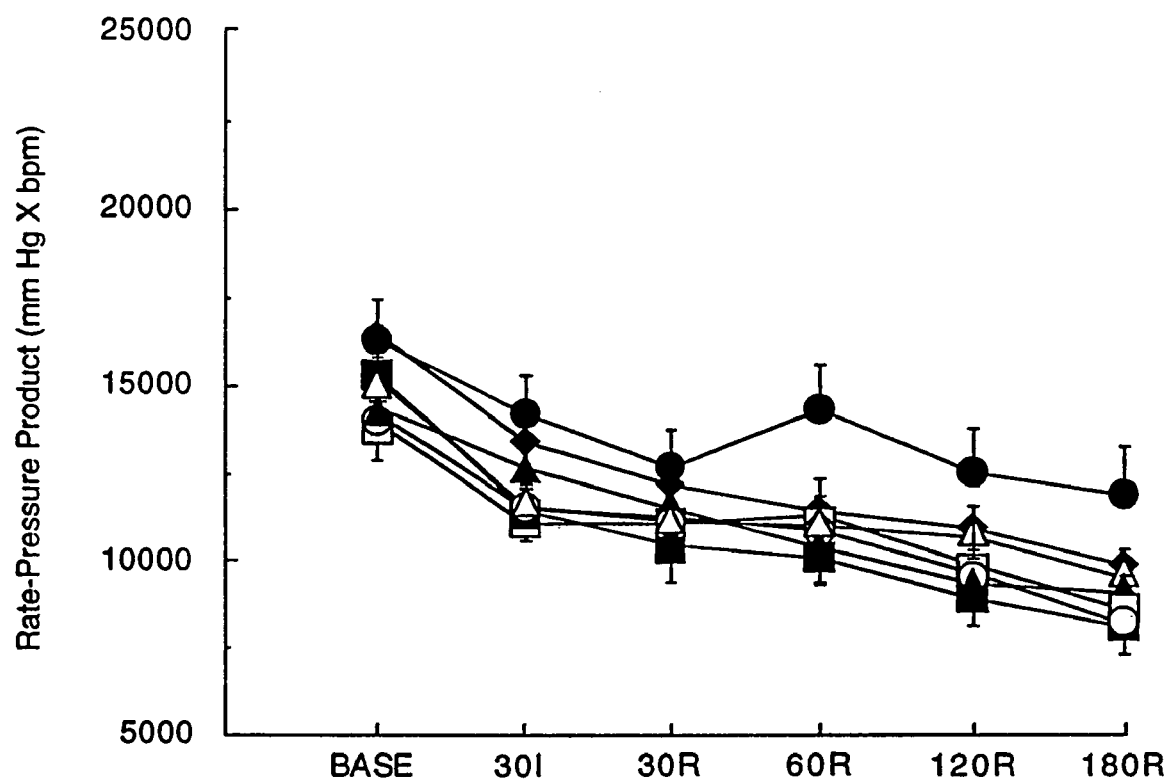

FIG. 16 is a graph of the heart rate-blood pressure product for rabbits during ischemia and reperfusion with or without heparinase treatment. The open circles and squares are data for saline pretreated and reperfusion treated rats, respectively. The open pyramids and solid circles are data for heparinase pretreated and reperfusion treated rabbits, respectively (25 ug/ml target plasma levels for heparinase III). The solid squares, pyramids and diamonds are data for heparinase reperfusion treated rabbits with 5, 1.25 and 0.25 ug/ml target plasma levels of heparinase III, respectively. BASE indicates baseline levels. 30I indicates the level at 30 minutes of ischemia. 30R, 60R, 120R and 180R indicates the levels at 30, 60, 120 and 180 minutes of reperfusion. The vertical lines indicate the standard deviation of the means.

Figure 17:
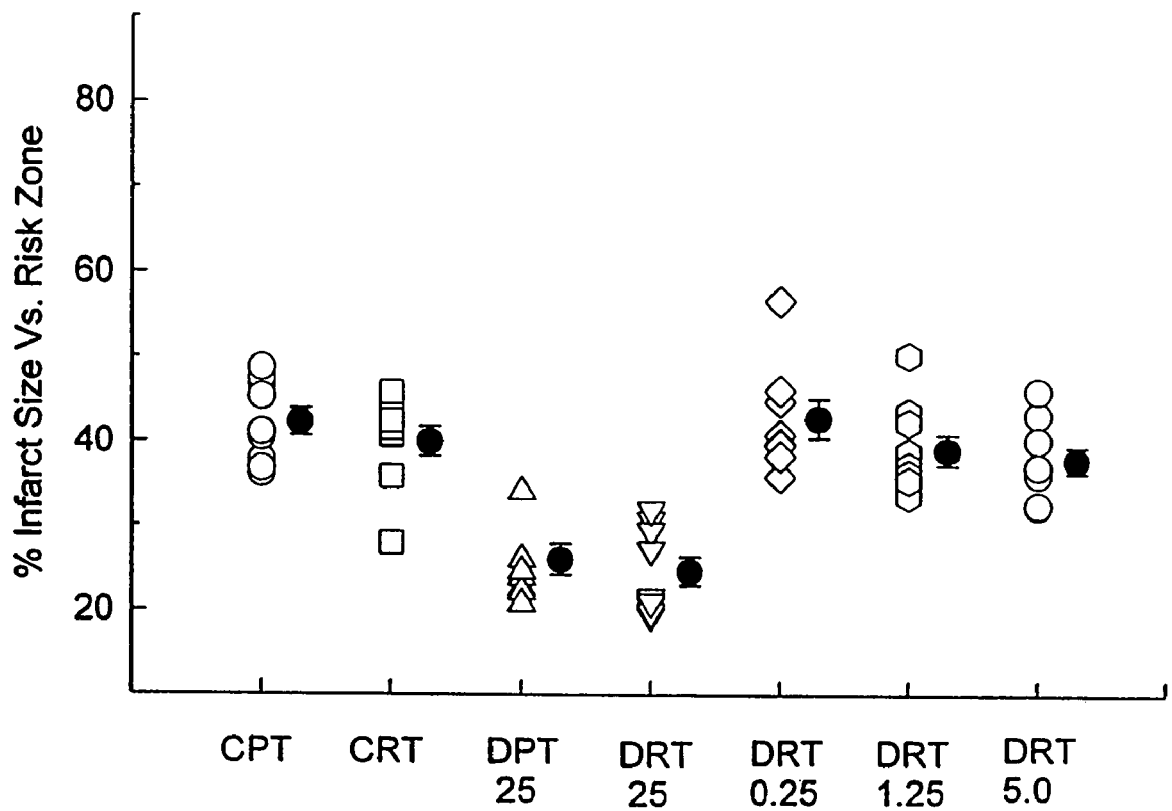

FIG. 17 is a graph of the percent of the infarct size vs. risk zone after ischemia and reperfusion in rabbit hearts, which underwent different heparinase treatments. The solid circles indicate the average levels for each treatment group. The open shapes indicate the levels for individual rabbits. CPT and CRT indicate saline pretreated and reperfusion treated rabbits, respectively. DPT and DRT indicate heparinase pretreated and reperfusion treated rabbits, respectively. The numbers below DPT and DRT indicate the target level of heparinase III in the plasma (in ug/ml). The vertical lines indicate the standard deviation of the means.

Figure 18:
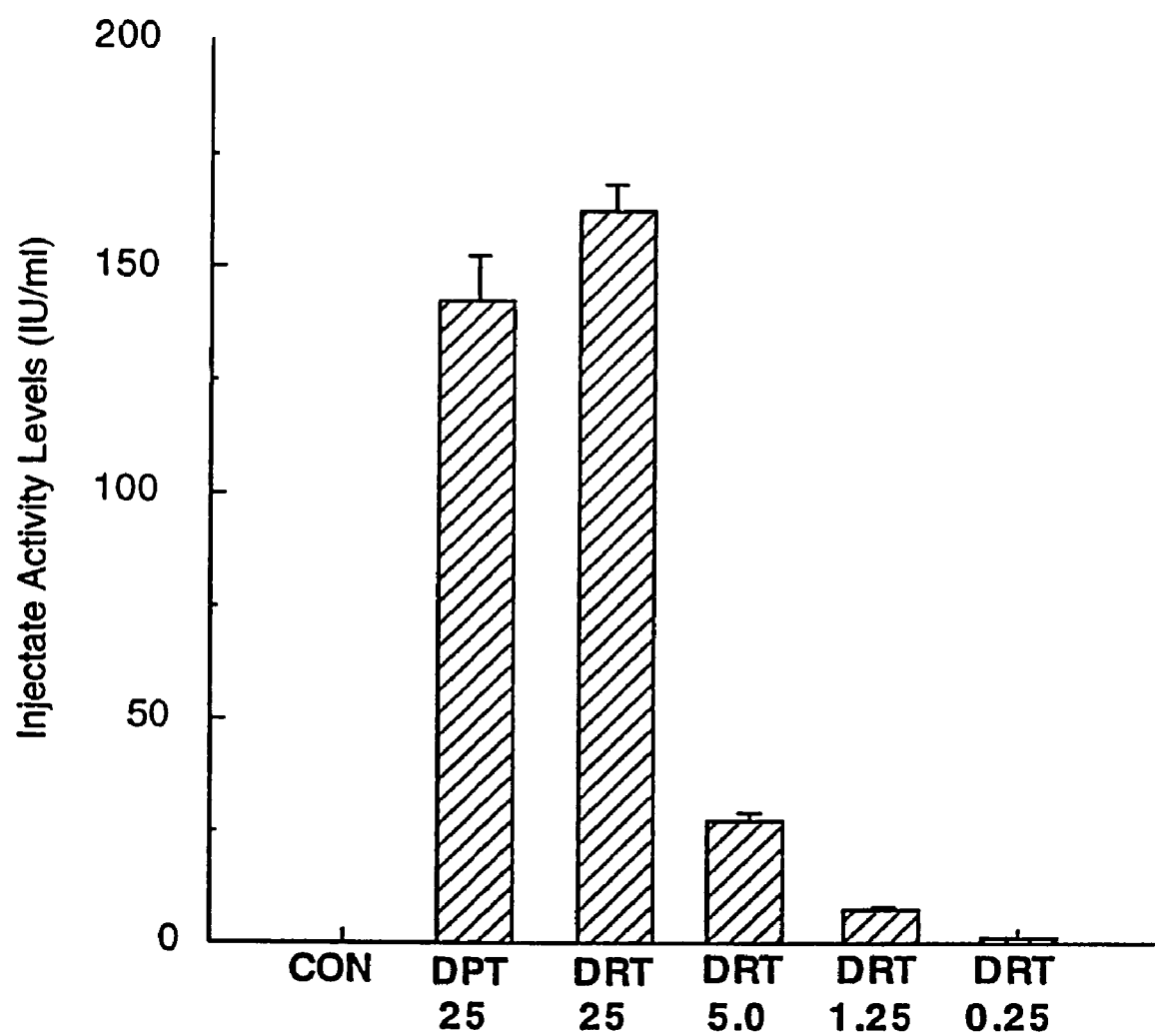

FIG. 18 is a graph of the concentration of heparinase III which was infused into the heparinase treated rabbits (in IU/ml). DPT and DRT indicate heparinase pretreated and reperfusion treated rabbits, respectively. The numbers below DPT and DRT indicate the target level of heparinase III in the plasma (in ug/ml). Con indicates control rabbits infused with saline. The vertical lines indicate the standard deviation of the means.

Figure 19:
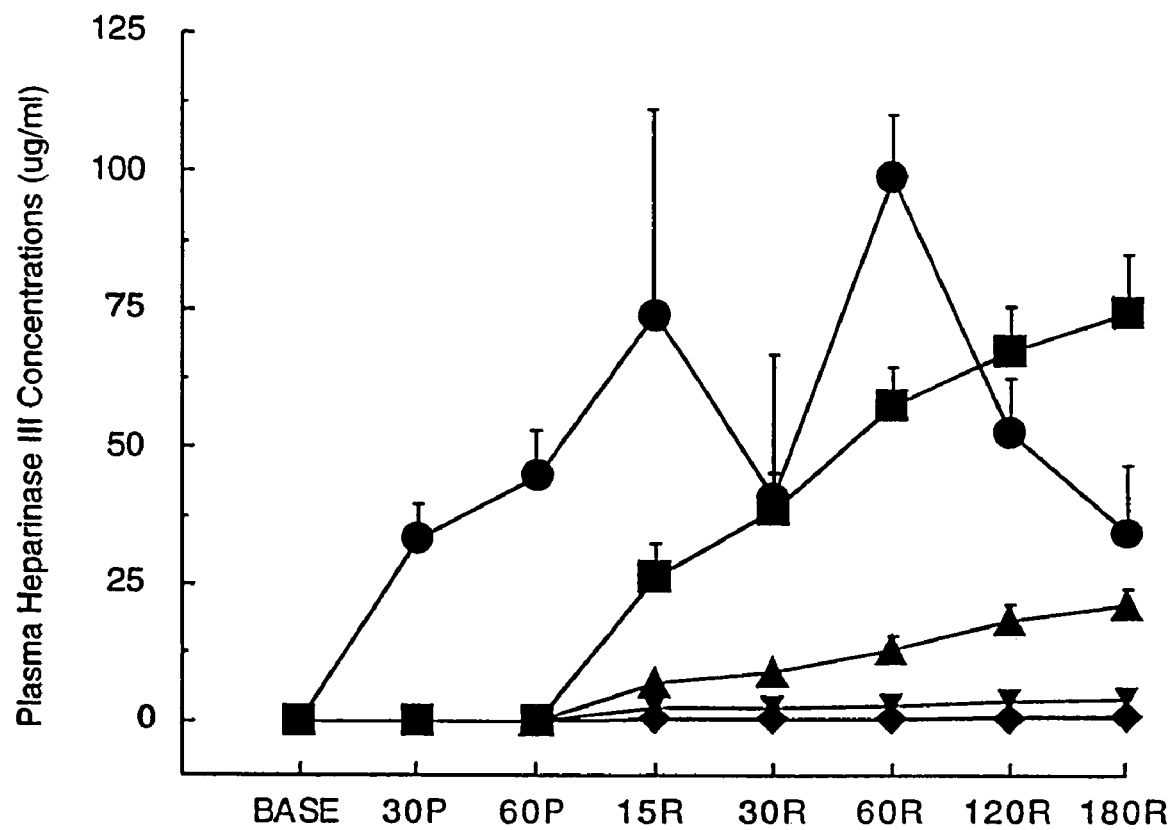

FIG. 19 is a graph of the concentrations of heparinase III measured in the rabbit plasma during pretreatment and reperfusion. The circles indicate the actual concentrations measured in heparinase pretreated rabbits targeted for 25 ug/ml plasma concentrations of heparinase III. The squares, pyramids, triangles and diamonds indicate the actual concentrations measured in heparinase reperfusion treated rabbits targeted for 25, 5, 1.25 and 0.25 ug/ml plasma concentrations of heparinase III, respectively. BASE indicates baseline concentrations. 30P and 60P indicate concentrations at 30 and 60 minutes of pretreatment. 15R, 30R, 60R, 120R and 180R indicate concentrations at 15, 30, 60, 120 and 180 minutes of reperfusion, respectively. The vertical lines indicate the standard deviation of the means.

DETAILED DESCRIPTION OF THE INVENTION

Interactions between leukocytes and endothelium are critical to the progress of localized inflammatory responses. These critical interactions include functional contacts between endothelium bound chemokines and leukocyte chemokine receptors, and between leukocyte L-selectin and heparin/heparan sulfate proteoglycans on endothelium. This invention is based on the discovery and is directed to the use of heparinase enzyme and heparinase fusion protein to decrease leukocyte-chemokine and leukocyte-endothelial cells proteoglycan interactions, and thereby inhibiting localized inflammation.

Heparin and heparan sulfate are glycosaminoglycan moieties of proteoglycans located on the surface of many different cell types and also found in the extracellular matrices produced by many cells. Endothelial cells produce extracellular matrix, primarily on their abluminal side, referred to as basement membrane. Endothelial cells, activated by certain cytokines or by other inflammatory response stimulators, increase their surface levels of heparin and heparan sulfate proteoglycans (excluding high endothelial venules), which act as inflammatory adhesion molecules, and interact with L-selectin on rolling leukocytes. This interaction increases contacts of leukocytes with the endothelium (increased rolling of leukocytes), which are necessary for subsequent steps in leukocyte recruitment. Activated endothelium also increases it's synthesis and secretion of chemokines. The secretion of chemokines in turn increases the localized concentration of the same chemokines, because the chemokines bind to is the heparin and heparan sulfate moieties of proteoglycans on the endothelial cells surfaces and in the basement membranes. This localized concentration gradient is required for activation of leukocytes for firm adhesion and extravasation, and results in leukocyte recruitment to inflammatory sites.

Heparinase enzymes have been found in microorganisms including *Flavobacterium heparinum* (Lohse and Linhardt, *J. Biol. Chem.* 267:2437-2455, 1992), *Bacteroides* strains (Saylers, et al., *Appl. Environ. Microbiol.* 33:319-322, 1977; Nakamura, et al., *J. Clin. Microbiol.* 26:1070-1071, 1988), *Flavobacterium* Hp206 (Yoshida, et al., 10th Annual Symposium of Glycoconjugates, Jerusalem 1989) and *Cytophagia* species (Bohn, et al., *Drug Res.* 41(I), Nr. 4:456-460, 1991). Heparanases from mammalian cells have also been described (Fuks, et al., U.S. Pat. No. 5,362,641, 1994; Hoogewerf et al., *J. Biol. Chem.* 270:3268-3277, 1995). The heparinases from *Flavobacterium heparinum*, heparinase I (EC 4.2.2.7), and heparinase II degrade heparin, while heparinase II also degrades heparan sulfate, as does heparinase III (EC 4.2.2.8). The products of complete digestion by these enzymes are mainly disaccharides, though small quantities of tetrasaccharides and oligosaccharides may persist. The enzymes can be used to remove cell surface and basement membrane glycosaminoglycans, heparin and heparan sulfate.

The removal of heparin and heparan sulfate from endothelial cells interferes with L-selectin interactions with endothelium, preventing increased leukocyte rolling. The removal of glycosaminoglycans from endothelial cells and basement membranes also removes glycosaminoglycan bound chemokines, which are critical for leukocyte recruitment. Loss of endothelial cells bound chemokines decreases activation of leukocyte integrins and inhibits firm adhesion by the leukocytes. It also inhibits extravasation of leukocytes, because the leukocytes require the presence of a bound gradient of chemokine for transmigration. It is believed, without being limited, that unbound chemoattractants are depleted from the endothelium layer by blood flow, preventing formation of a significant soluble chemoattractant gradient.

Generally, after a one hour heparinase treatment, 50% of the digested cell surface and basement membrane heparin and heparan sulfate are replaced within 2 to 4 hours, and it is completely replaced within 12 to 16 hours. Longer treatment times (3 and 5 hours) greatly extended the time needed to replace the same amount of heparin/heparan sulfate. Inflammatory responses would be significantly diminished by a slow rate of replacement of cell surface heparin/heparan sulfate. Appropriate administration of heparinase could extend the duration of diminished inflammatory response.

PREPARATION OF HEPARINASE

Individual heparinases or a combination thereof, that may be used in this invention can be prepared from a variety of sources. Heparinase may be prepared by isolation from bacterial or mammalian cells, either those which, naturally produce the enzymes or have been genetically engineered to produce the enzymes as described in by known methods. In addition, mammalian heparanases from human cells may be isolated according to procedures for purification described by Fuks, et al. (U.S. Pat. No. 5,362,641, 1994).

Isolation of Heparinases from *Flavobacterium Heparinum*

Heparinase enzymes can be purified from cultures of *Flavobacterium heparinum* as follows. *F. heparinum* is cultured in 15 L computer controlled fermenters, in a variation of the defined nutrient medium described by Galliher et al., *Appl. Environ. Microbiol.* 41(2):360-365, 1981. For fermentations designed to produce heparin lyases, semi-purified heparin (Celsus Laboratories) is included in the media at a concentration of 1.0 g/L as the inducer of heparinase synthesis. The cells are harvested by centrifugation and the desired enzymes released from the periplasmic space by a variation of the osmotic shock procedure described by U.S. Pat. No. 5,169,772 to Zimmermann, et al. (1992).

Proteins from the crude osmolate are adsorbed onto cation exchange resin (CBX, J. T. Baker) at a conductivity of between one and seven mhos. Unbound proteins from the extract are discarded and the resin packed into a chromatography column (5.0 cm i.d.×100 cm). The bound proteins elute at a linear flow rate of 3.75 cm·min−1 with step gradients of 0.01 M phosphate, 0.01 M phosphate/0.1 M sodium chloride, 0.01 M phosphate/0.25 M sodium chloride and 0.01 M phosphate/1.0 M. sodium chloride, all at pH, 7.0±0.1. Heparinase II elutes in the 0.1 M NaCl fraction while heparinases, I and III, elute in the 0.25 M fraction. Alternately, the 0.1 M sodium chloride step is eliminated and the three heparinases co-eluted with 0.25 M sodium chloride. The heparinase fractions are loaded directly onto a column containing cellufine sulfate (5.0 cm i.d.×30 cm, Amicon) and eluted at a linear flow rate of 2.50 cm·min−1 with step gradients of 0.01 M phosphate, 0.01 M phosphate/ 0.2 M sodium chloride, 0.01 M phosphate/0.4 M sodium chloride and 0.01 M phosphate/1.0 M. sodium chloride, all at pH, 7.0±0.1. Heparinases II and III elute in the 0.2 M sodium chloride fraction while heparinase I elutes in the 0.4 M fraction. The 0.2 M sodium chloride fraction from the cellufine sulfate column is diluted with 0.01 M sodium phosphate to give a conductance less than 5 mhos. The solution is further purified by loading the material onto a hydroxyapatite column (2.6 cm i.d.×20 cm) and eluting the bound protein at a linear flow rate of 1.0 cm·min−1 with step gradients of 0.01 M phosphate, 0.01 M phosphate/0.35 M sodium chloride, 0.01 M phosphate/0.45 M sodium chloride, 0.01 M phosphate/0.65 M sodium chloride and 0.01 M phosphate/1.0 M sodium chloride, all at pH, 7.0±0.1. Heparinase II elutes in a single protein peak in the 0.45 M sodium chloride fraction while heparinase III elutes in a single protein peak in the 0.65 M sodium chloride fraction. Heparinase I is further purified by loading material from the cellufine sulfate column, diluted to a conductivity less than 5 mhos, onto a hydroxyapatite column (2.6 cm i.d.×20 cm) and eluting the bound protein at a linear flow rate of 1.0 cm·min−1 with a linear gradient of phosphate (0.01 to 0.25 M) and sodium chloride (0.0 to 0.5 M). Heparinase I elutes in a single protein peak approximately mid-way through the gradient.

The heparinase enzymes obtained by this method are greater than 98.5% pure as estimated by reverse phase HPLC analysis (BioCad, POROS II). Purification results for the heparinase enzymes are shown in Table A.

TABLE A

Purification of heparinase enzymes from *Flavobacterium heparinum* fermentations

| sample | activity (IU) | specific activity (IU/mg) | yield (%) |
|---|---|---|---|
| fermentation | | | |
| heparin degrading | 94,500 | | 100 |
| heparan sulfate degrading | 75,400 | ND | 100 |
| osmolate | | | |
| heparin degrading | 52,100 | | 55 |
| heparan sulfate degrading | 42,000 | ND | 56 |
| cation exchange | | | |
| heparin degrading | 22,600 | | 24 |
| heparan sulfate degrading | 27,540 | ND | 37 |
| cellufine sulfate | | | |
| heparin degrading | 19,200 | | 20 |
| heparan sulfate degrading | 9,328 | 30.8 | 12 |
| hydroxylapatite | | | |
| heparinase 1 | 16,300 | 115.3 | 17 |
| heparinase 2 | 2,049 | 28.4 | 3 |
| heparinase 3 | 5,150 | 44.5 | 7 |

Isolation of Recombinant Enzymes

Glycosaminoglycan degrading enzymes also can be isolated from recombinant expression systems such as the heparinase I expression system described by Sasisekharan, et al., *Proc. Natl. Acad. Sci. USA* 90:8660-8664, 1993; the heparinase, II and III, expression systems described in co-pending U.S. patent application Ser. No. 08/258,639, "Nucleic Acid Sequences and Expression Systems for Heparinase II and Heparinase III Derived From *Flavobacterium heparinum*" by Su, et al., filed Jun. 10, 1994, the teachings of which are incorporated herein. In these expression systems, the *F. heparinum* genes are isolated and cloned into plasmids downstream from an inducable promoter. The plasmids are introduced into *E. coli* and the expression of the desired enzyme directed by a suitable induction method such as temperature shift or addition of IPTG to the medium.

The enzymes can be recovered in a purified form by a modification of the methods described herein. Cell disruption is achieved by homogenization, sonication or enzymatic treatment to break the cell wall and release cytoplasmic components. If enzyme synthesis results in aggregation, the aggregate can then be dissolved by a denaturing agent, 3 to 6 M guanidine HCl or 4 to 8 M urea and the protein refolded by removal of the denaturing agent through dialysis or dilution. The refolded enzyme can be further purified using the liquid chromatographic methods described above.

Construction of Fusion Proteins

Fusion proteins incorporating heparinase enzyme fused to proteins with specific binding properties can be created by recombinant molecular biology techniques. By choosing an appropriate binding protein, heparinase activity can be targeted to specific sites, in vivo. ICAM-1 has been shown to be preferentially expressed on the surface of activated endothelial cells: (Dustin, et al., J. Immunol., 137:245-254, 1986). As examples of fusion proteins; an antibody, Fab fragment or variable region, specific for ICAM-1, VCAM-1 or P-selectin, when fused to heparinase enzyme or an active portion thereof, localizes heparinase activity near the luminal and abluminal surfaces of activated endothelium. Heparin and heparan sulfate moieties are removed in this area, causing breakdown of the chemokine gradient produced by the endothelium. As other examples, fusion of heparinase enzyme, or an active portion thereof, to the I-domain of LFA-1 or Mac-1 (both bind to ICAM-1) targets activated endothelium for removal of heparin and heparan sulfate, inhibiting leukocyte rolling and chemokine gradient formation. Receptors for cytokines such as IL-1b, are up-regulated on activated endothelium and provide another target for binding of fusion proteins. By fusing IL-1b, or the receptor binding domain of IL-1b to heparinase targeting can also be achieved. The fusion proteins can decrease inflammatory responses at lower blood concentrations than is required for comparable decreases using unfused heparinase. In addition, other cells in the vascular system will be less affected by the enzyme activity of the fusion protein, reducing possible side effects of treatments.

Heparinase fusion proteins created by genetic engineering retain the binding and catalytic properties of heparinase and of the protein to which it is fused. Three heparinases have been purified to homogeneity from *Flavobacterium heparinum,* and have been produced in a recombinant form in *Escherichia coli*. Fusion proteins consisting of heparinase enzyme combined with binding domains from antibodies or adhesion molecules can be produced with a gene fusion in a recombinant host, while retaining the functionalities of binding and the enzymatic activity of the separate proteins. These molecules can also be purified to homogeneity by procedures normally used for purification of the individual parts of the fusion protein (e.g. affinity chromatography, heparinase purification protocols). Unlike the natural heparinase purified from *Flavobacterium heparinum*, the recombinant enzyme may not contain amino-terminal pyroglutamate or carbohydrate moieties. All recombinant heparinase may contain deletions, additional and/or altered amino acids, which modify the enzymatic activity of the natural enzyme or the functioning of the binding domains.

Heparinase and fusion heparinase can be stabilized for in vivo use, by complexing with polyethylene glycol, cross linking agents, and by microencapsulation.

For example, the gene for heparinase I was isolated from *F. heparinum* as described by Sasisekharan, et al., *Proc. Natl. Acad. Sci.* 90:3660-3664, 1993, and an EcoRI restriction site was inserted 5' to the codon encoding the glutamine-21 residue by polymerase chain reaction. A fragment containing the heparinase I gene was prepared by digestion with restriction endonucleases; EcoRI and BamHI, and ligated to the EcoRI/BamHI cleaved pMALc2 plasmid (New England Biolabs). The resulting plasmid contained a hybrid gene encoding a 82,000-85,000 Dalton protein incorporating the maltose binding protein (MalB) fused 5' to the heparinase I gene. This plasmid was inserted into *Escherichia coli* HB101 cells using the calcium chloride mediated method described by Cohen et al., *Proc. Natl. Acad. Sci.* 69:2110-2111. These cells exhibited heparinase activity under the control of the tac promoter, allowing synthesis of the fusion protein by addition of 0.1 mM of the inducing agent IPTG to the growth medium.

The HB101(pMALc2-HEP1Q21) cells were grown to a cell density of 1.0 g/L dry cell weight in 500 ml, M9 medium containing 0.1 mM IPTG at 37° C. and concentrated by centrifugation, 10,000 g×10 minutes. The cell pellet was suspended in 10 ml 0.025 M Tris, pH 7.7, and the cells disrupted by sonication using a Heat Systems Model XL2020, 4.5 minutes, power level 3, 30 second on 30 second off cycles. Cell debris was removed by centrifugation, 10,000 g×10 minutes, and the supernatant applied to an amylose affinity resin column (1.0 i.d.×2 cm, New England Biolabs). The bound protein was eluted with a step gradient of 0.025 M Tris containing 0.01 M maltose at pH 7.5. The fusion protein eluted in a protein peak which displayed a heparinase specific activity of 23.77 IU/mg.

The heparinase-maltose binding fusion protein also can be purified by standard protein separation techniques based on heparinase properties. Cell sonicates were fractionated by ammonium sulfate precipitation. Non-specific proteins were removed with a precipitation step at 1.7 M ammonium sulfate and the supernatant precipitated by raising the ammonium sulfate-concentration to 3.2 M. The precipitated material contained the fusion protein and was resuspended in 0.025 M sodium phosphate, pH 6.5. The material was applied to a weak cation exchange column (1.6 i.d.×10 cm, CBX, J. T. Baker) and eluted with sequential step gradients of 0.0 M sodium chloride, 0.01 M sodium chloride, 0.25 M sodium chloride and 1.0 M sodium chloride, all in 0.025 M sodium phosphate. The fusion protein eluted in the 0.25 M sodium chloride elution fraction and displayed a heparinase specific activity of 29.95 IU/ml. These two purification procedures demonstrate that functional heparinase fusion proteins can be made by genetically linking a protein with desired binding properties to the N-terminal end of heparinase and the resulting fusion protein retains the functionality of both heparinase and the protein to which it is fused.

As another example of a fusion protein, a BamHI/SalI restriction fragment from pGBH3, which contains the heparinase III gene from *Flavobacterium heparinum* was inserted into pMALc2 to form a gene for fusion of a maltose binding protein with heparinase II. Extracts of the *E. coli* strain DH5a containing the fusion gene plasmid were produced as described in the last example, and these extracts contained 18.7 IU/ml/O.D. of heparinase III activity. The extract was also combined with amylose affinity resin and the resin was then separated from the extract by centrifugation. The resin was washed once with 0.025M Tris (pH 7.5) solution and proteins bound to the resin were resuspended in SDS-PAGE sample buffer and separated according to size on a 7.5% SDS-polyacrylamide gel. Western blot analysis of the gel with anti-heparinase III specific antibody identified a 116,000 Da. protein, which corresponds to the expected size of the fusion protein. This analysis indicates that the fusion protein has a functional maltose binding domain. This example demonstrates that the heparinase III protein can also be fused to a binding domain to produce a bifunctional fusion enzyme.

Protection of Proteins In Vivo

Methods for extending the in vivo half-life are known and routinely used, especially in the case of enzymes. One example of a suitable method is the attachment of polyethylene glycol moieties to the protein, which inhibits uptake by the reticuloendothelial system. Preparation and characterization of such non-immunogenic proteins is described by Lu, et al. (*Pept. Res.* 6(3), 140-146, 1993), Delgado, et al. (*Critical Rev. Ther. Drug Carrier Syst.* 9(3-4), 249-304, 1992) and Davis et. al. (U.S. Pat. No. 4,179,337, 1979), the teachings of which are incorporated herein. Another example of a suitable method is the use of bifunctional cross-linking agents to stabilize the enzyme against proteolytic degradation. Glutaraldehyde is one type of bifunctional cross-linking agent. PCT WO95/00171, by Novo Nordisk A/S contains a listing of other useful bifunctional cross-linking agents, and teaches the use of these, which is incorporated herein.

PREPARATION OF PHARMACEUTICAL COMPOSITIONS

Heparinase enzyme can be administered either locally or systemically. Local administration can provide greater control. Heparinase is mixed with an appropriate pharmaceutical or veterinary carrier, then administered in an effective amount to produce the desired effect on the treated cells using methods known to those skilled in the art, for example, for local application, use of perfusion, injection or a catheter.

Targeting and effective concentration dosages can be achieved by preparation of targeted enzymes as described above, or by the use of targeting vehicles, such as a catheter or localized injection, to achieve controlled site specific delivery of enzyme.

Administration of Enzymes via Controlled Release Matrices or Injection

Heparinase enzyme can be formulated in a carrier for administration by injection, for example, in saline or an aqueous buffer, using standard methodology, or encapsulated in a polymeric matrix. Encapsulation of heparinase in controlled release formulations is well known; materials include but not limited to liposomes, lipospheres, biodegradable polymeric matrices, and vesicles. These encapsulants are typically microparticles having a diameter from 60 nm to 100 microns, but preferably less than ten microns, and more preferably one micron or less in diameter.

Proteosomes are prepared from outer membrane proteins of the *Meningococcal* bacteria and been reported to bind proteins containing hydrophobic anchors by Lowell, et al., *Science,* 240:800 (1988). Proteosome proteins are highly hydrophobic, reflecting their role as transmembrane proteins and porins. When isolated, their hydrophobic protein-protein interactions cause them to form naturally multimolecular, membranous 60 to 1000 nm vesicles or membrane vesicle fragments, depending on the strength of the detergent used in their isolation. Heparinase can also be encapsulated within a proteoliposome as described by Miller et al., *J. Exp.*

Med. 176:1739-1744 (1992) and incorporated by reference herein, as described above with reference to proteosomes. Alternatively, heparinase can be encapsulated in lipid vesicles such as Novasome™ lipid vesicles (Micro Vescular Systems, Inc., Nashua, N.H.). Another carrier is described in PCT US90/06590 by Nova Pharmaceuticals, the teachings of which are incorporated herein, which is referred to as a liposphere, having a solid core and an outer shell layer formed of phospholipid.

The carrier may also be a polymeric delayed release system. Biodegradable synthetic polymers are particularly useful to effect the controlled release of heparinase. Microencapsulation has been applied to the injection of microencapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters and polyamides, particularly those that are biodegradable.

A frequent choice of a carrier for pharmaceuticals is poly (d,l-lactide-co-glycolide) (PLGA). This is a biodegradable polyester that has a long history of medical use in erodible sutures, bone plates and other temporary prostheses, where it has not exhibited any toxicity. A wide variety of pharmaceuticals including peptides and antigens have been formulated into PLGA microcapsules. The PLGA microencapsulation process uses a phase separation of a water-in-oil emulsion. Heparinase is prepared as an aqueous solution and the PLGA is dissolved in a suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, polyvinylpyrrolidone (PVP, methyl cellulose) and the solvent removed by either drying in vacuo or solvent extraction. Other means for encapsulation include spray drying, co-precipitation, and solvent extraction.

Means for Administration

Heparinase enzyme can be administered by injection, infusion or perfusion. Typically, injection is performed using either a syringe or catheter. Either a syringe or a catheter can be used to apply heparinase locally to areas of blood vessels, tissues or organs. Patients diagnosed with localized inflammations can be treated by introduction of heparinase into their vascular system by these means. Heparinase can also be administered before or simultaneously with surgery, to reduce resulting inflammatory responses. In addition, preceding transplant surgery, the donor organ can be perfused with a heparinase preparation to reduce inflammation upon reperfusion after transplantation.

The present invention will be further understood by reference to the following non-limiting examples.

EXAMPLES

Example 1

Treatment of Endothelial Cells with Heparinase to Release Heparin/Heparan Sulfate Heparinase alters the cell surface and basement membrane by cleaving the heparin and heparan sulfate moieties from the cell surface and extracellular matrix proteoglycans. Removal of these glycosaminoglycans will decrease leukocyte-endothelium interactions (leukocyte rolling) by decreasing binding of L-selectin on leukocytes to endothelium proteoglycans. In addition, the removal of heparin and heparan sulfate will decrease binding of chemokines to the endothelium, which will reduce leukocyte activation, sticking and extravasation. Production of bovine corneal endothelial cells with 35S-heparin/heparan sulfate proteoglycans and subsequent digestion of these radiolabeled proteoglycans with *Flavobacterium* heparinase III provides a qualitative assessment of the effect of the enzyme on the cell surface. Digestion of cell surface proteoglycans with heparinase III will release both heparin and heparan sulfate moieties, because these moieties are interspersed on the same unbranched carbohydrate chains. Significant quantities of $^{35}$S-heparin/heparan sulfate were solubilized by the heparinase III treatment.

$^{35}$S-sulfate containing endothelial cell layers were produced by seeding 24 well dishes with primary bovine corneal endothelial cells. These were grown until 1 day prior to confluence in DMEM with 10% fetal calf serum and 5% calf serum. One day prior to confluence the cells were diluted 10-fold into Fisher medium supplemented with 10% fetal calf serum, 5% calf serum, 4% dextran, and 25 mCi/ml Na$_2$35SO$_4$ and cultured for 3 days with the addition of 0.5 ng/ml per day bFGF. Incorporation of label by near-confluent cells localizes the label in and on the cell and minimizes the $^{35}$S-label incorporated into the basement membrane.

Endothelial cell layers containing $^{35}$S-sulfate were treated with 600 ul phosphate buffered saline or heparinases III, in phosphate buffered saline, at a concentration of 1.0 IU/ml, in duplicate wells. The digestions were allowed to proceed for 5, 30 or 60 minutes at 37° C. After the indicated time of digestion, 400 ul of digestion solution was removed from each well and fractionated on a Bio-sil SEC 125-5 gel filtration column controlled by a Beckman System Gold HPLC, equipped with an autosampler. The flow rate was 1 ml/minute and 1 ml fractions were collected. The amount of 35S-sulfate present in each fraction was determined by measuring an aliquot of each fraction on a Packard 1600 TR liquid scintillation counter. The labeled, untreated control solutions were fractionated and measured in the same manner, and the quantity of radioactive material in each fraction (background) was subtracted from the amount present in fractions from the heparinase digested samples. The amount of cell surface $^{35}$S-labeled heparin/heparan sulfate in each fraction released by heparinase III treatment is shown in FIG. 1.

Example 2

Determination of the Extent of Removal and the Rate of Replacement of Heparin/Heparan Sulfate Moieties on Endothelial Cells and in Basement Membranes Treated with Heparinase The growth factor, basic Fibroblast Growth Factor (bFGF), is a well characterized heparin binding protein, which is known to bind to the heparin moieties of proteoglycans on the cell surface, and in the extracellular matrix (Maccarana, et al., *J. Biol. Chem.*, 268:23898-23905, 1993). Binding of $^{125}$I-labeled bFGF to cell surface and basement membrane proteoglycans was used to access the amount of heparin/heparan sulfate removed from unactivated and IL-1b activated endothelial cell layers and their basement membranes by heparinases I, II or III. Digestion of the cell surface and basement membrane with heparinase will remove both heparin and heparan sulfate moieties, because these moieties are interspersed on the same unbranched carbohydrate chains. $^{125}$I-labeled bFGF binding was also used in this experiment to determine the rate at which heparin/heparan sulfate moieties were replaced on the cell surface and basement membrane of endothelium treated with heparinases I, II or III.

Figure 2:
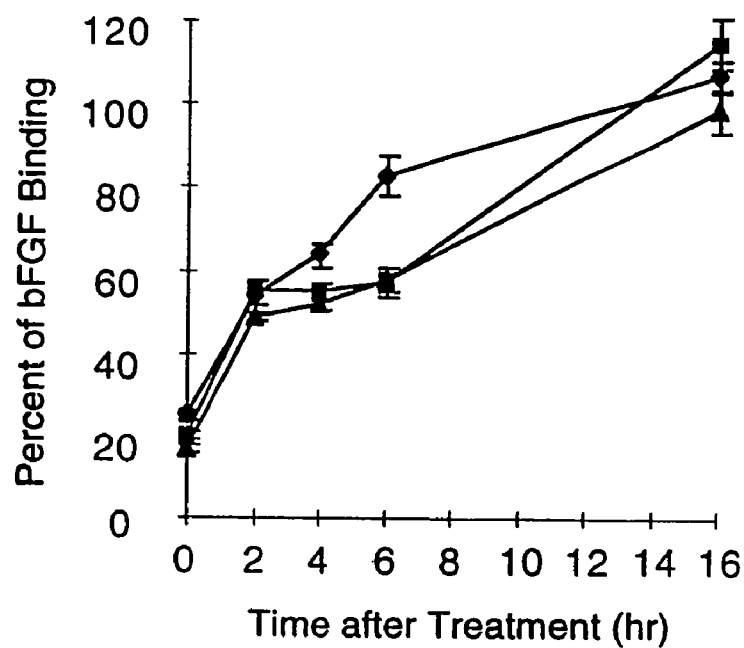
Figure 2:
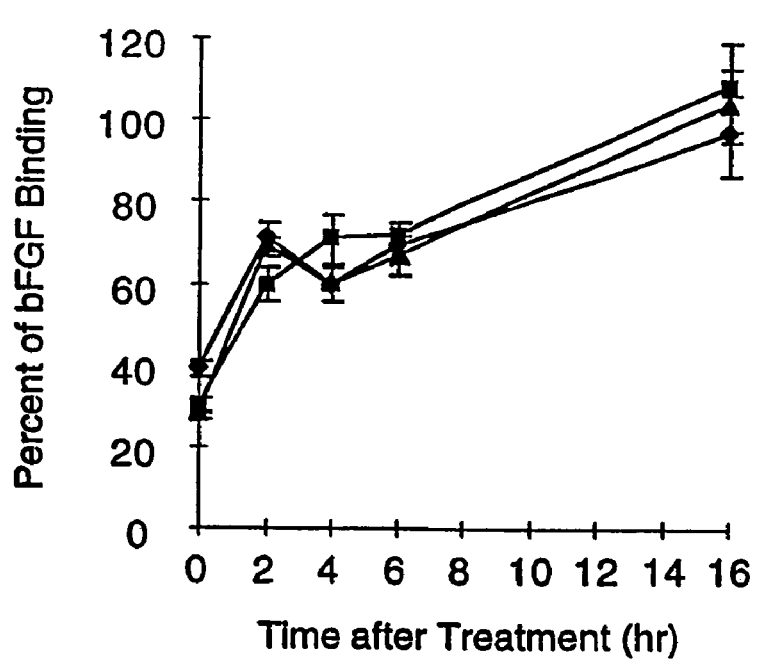
Figure 3:
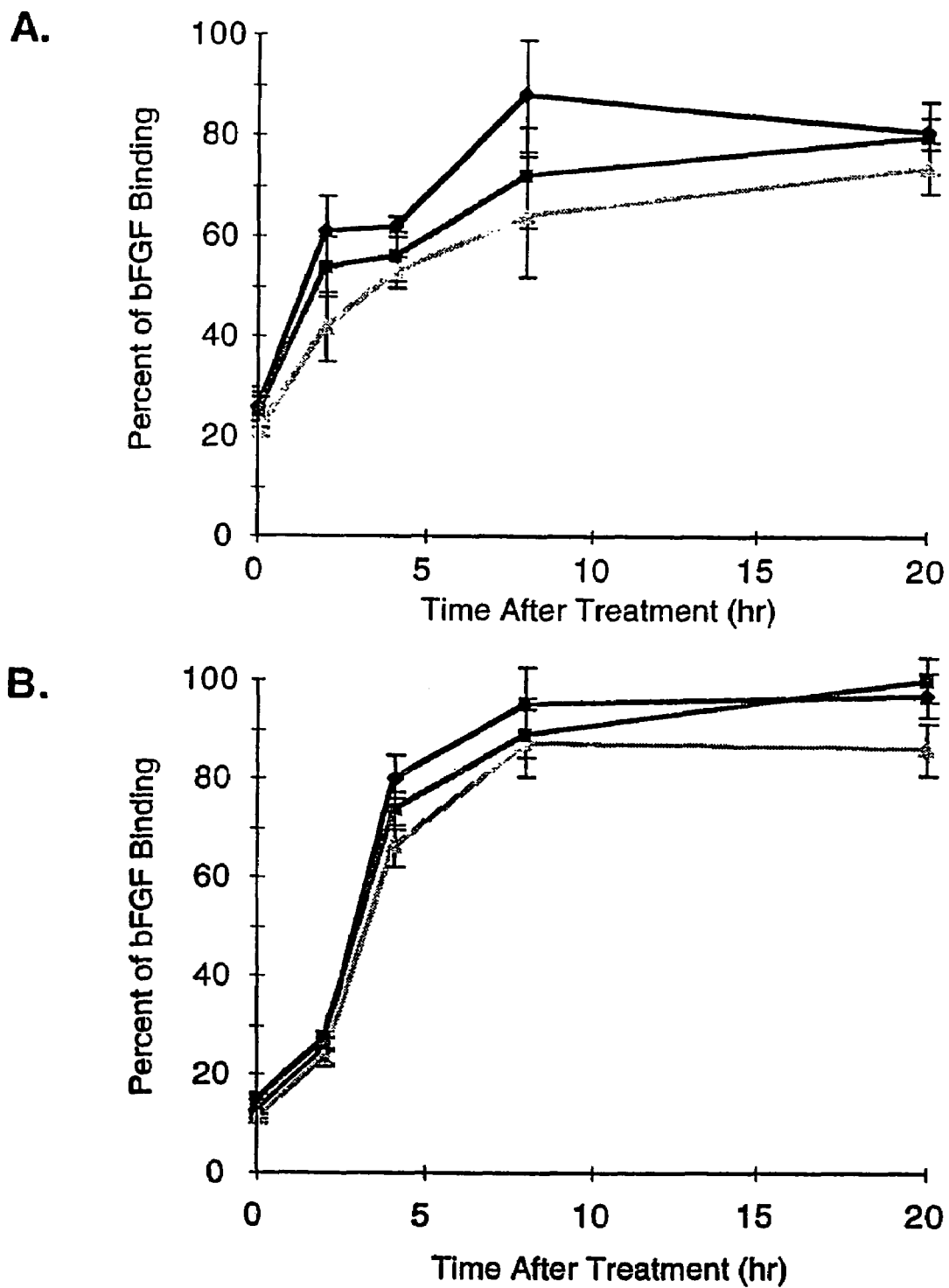
Figure 4:
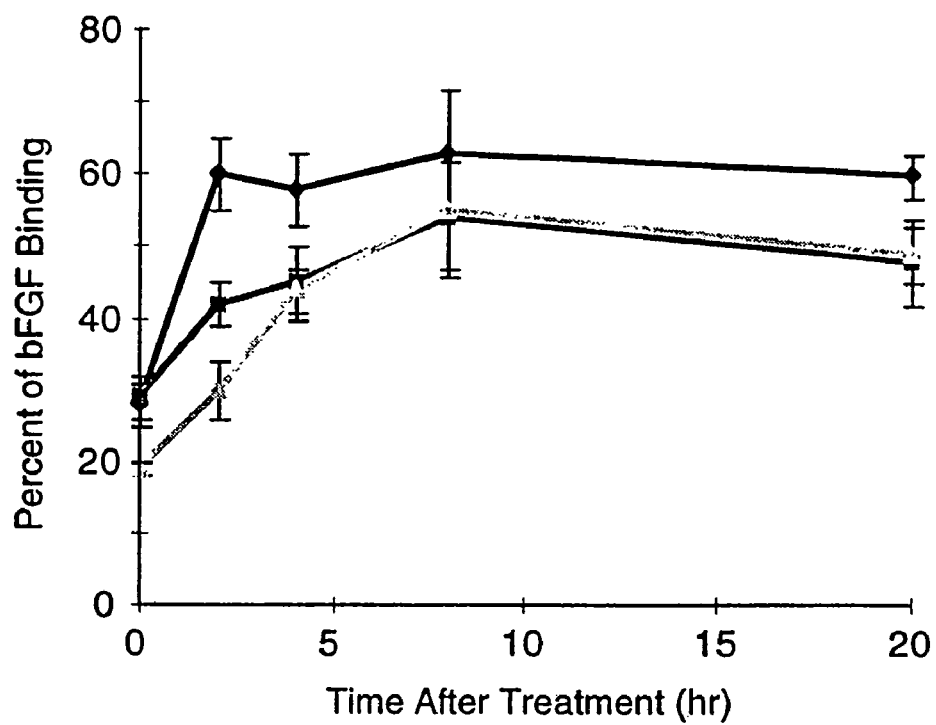
Figure 4:
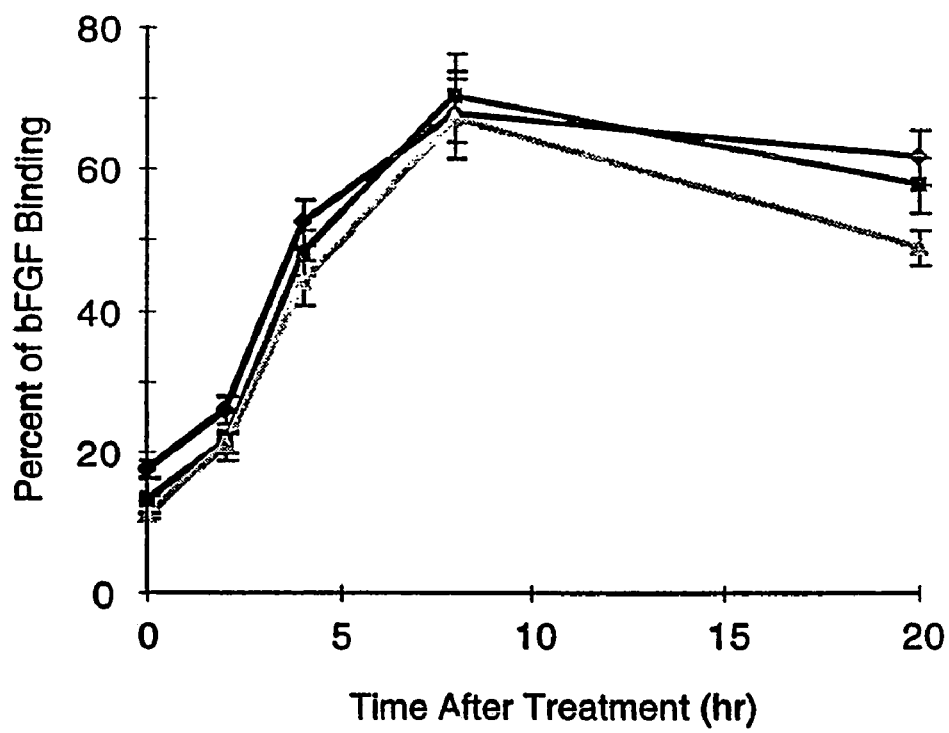

Most of the heparin/heparan sulfate can be removed using heparinase (70 to 90%; FIGS. 2, 3 and 4). This demonstrates that the endothelium can be almost completely depleted of heparin/heparan sulfate moieties by use of heparinase. With a 1 hour heparinase treatment the rate of replacement of the heparin/heparan sulfate is generally biphasic in nature. Replacement of 40 to 50% of the digested heparin/heparan sulfate occurs within a few hours. Additional replacement of the depleted heparin/heparan sulfate occurs at a slower rate during the remainder of the experiment, with complete replacement occurring 12 to 16 hours. 3 and 5 hour treatments with heparinases caused slower rates of replacement of heparin/heparan sulfate on the cell surface (FIGS. 3 and 4). This was most evident for unactivated endothelium. For the experimental results depicted in FIGS. 3 and 4 for the IL-1 activated endothelium, all three treatment times (1, 3, and 5 hours) gave lower replacement rates than was observed in the experimental results depicted in FIG. 2.

This data indicates that significant inhibition of L-selectin binding and immobilized chemokine gradient formation will result from heparinase treatment, and this would result in significant inhibition of localized inflammatory responses. Also, a treatment period of 3 to 5 hours can greatly extend the period of diminished inflammatory response by decreasing the rate of heparin/heparan sulfate replacement.

A human endothelial cell line was grown to confluency in 48 well dishes in 0.25 ml/well of RPMI medium, containing; 1% penicillin/streptomycin, and 20% fetal serum. Cells in half of the wells were activated for 4 hours with 10 ul of 50 ng/ml IL-1b. After activation all wells were washed 3 times with HBSS and treated with either Incubation Medium (RPMI medium, 25 mM Tris HCL pH 8, 25 mM HEPES pH 7.4, and 0.1% BSA) or 0.1 IU/ml of heparinase I, II or III diluted in Incubation Medium, at 37° C., in 5% $CO_2$, for 60 min for experimental results depicted in FIG. 2, or for the results depicted in FIGS. 3 and 4, 1.0 IU/ml heparinase I or III diluted in Incubation Medium, at 37° C., in 5% $CO_2$, for 60 min with none, 3 or 5 replacements of the enzymes every hour. After enzyme treatments, the wells were washed 3 times with HBSS and incubated with RPMI medium, containing; 1% penicillin/streptomycin and 20% fetal serum, ±IL-1b, at 37° C., in 5% $CO_2$, for the times indicated in FIG. 2. The wells were again washed 3 times with HBSS and 0.1 ml of Incubation Medium was added to each well, and the plates were cooled on ice for 5 min. To all of the wells was added 20 ul of 125 ng/ml $^{125}$I-bFGF, and 20 ul of 20 ug/ml unlabeled bFGF. To some of the control wells, 15 ul of 10 mg/ml heparin was also added, to determine nonspecific background binding. The plates were incubated on ice for 40 minutes and washed 2 times with cold HBSS. 0.25 ml of LAB (25 mM HEPES pH 7.4 and 2 M NaCl) was added to each well to solubilize the bFGF, and then it was collected in tubes. This step was repeated, and the contents of the tubes were counted in a gamma counter. The amount of nonspecific background binding was subtracted from each untreated control and treated sample. The sample counts were divided by the control counts to determine the percent of binding that occurred. The results ± standard errors (SE) are shown in FIGS. 2, 3 and 4.

Example 3

Treatment of Activated Endothelial Cell Layers and Basement Membranes with Heparinase to Release Heparin/Heparan Sulfate Bound Chemokine, IL-8

Removal of the bound chemokine gradient formed by activated endothelium adjacent to inflamed tissue will inhibit the accumulation of neutrophils within this tissue, and will decrease the inflammatory response. The chemokine, IL-8, is produced by endothelium activated by IL-1b and other cytokines and chemoattractants, which are secreted by inflamed tissues. If IL-8 bound to endothelium can be solubilized by treatment with heparinase, then it would be removed from the area of inflammation by blood flow and the localized inflammatory response would be inhibited. The in vitro removal and solubilization of 0.5 to 3 fold more endogenous, immobilized IL-8 (vs. secreted IL-8) from activated endothelium by heparinases I, II or III, or by heparinases I and III demonstrates that the bound chemokine gradient can be destroyed by heparinase treatment.

One ml of a 3 mg/ml solution of human collagen was used to coat the wells of a 12 well plate. Any remaining collagen solution was removed by aspiration. Human umbilical venous endothelial cells (HUVEC; used at passages 1 to 8) from a confluent 10 ml plate were trypsin treated, and diluted 1 to 7 in RPMI medium containing; 20% fetal serum, 1% penicillin/streptomycin, 100 ug/ml heparin, 10 ug/ml of epidermal growth factor and 200 ug/ml of endothelial cell growth supplement. One ml of diluted cells was added to each well of the collagen coated 12 well plates. The cells were grown until confluent, at 37° C., in 5% $CO_2$. The culture medium was changed every other day during the growth period. The day before the chemokine assay the medium was exchanged for 1 ml of RPMI medium without heparin.

To activate the endothelium layer, 50 ng/ml of human recombinant IL-1b, diluted in RPMI medium (minus fetal serum, epidermal growth factor, endothelial cell growth supplement and heparin) and 2% BSA was added to non-control wells to a final concentration of 2 ng/ml. The multiwell plates were incubated at 37° C., in 5% $CO_2$, for 4 hours. The medium was removed from all of the wells and the wells were washed two times with Hanks Balanced Salt Solution (HBSS). 0.5 ml of RPMI medium (minus fetal serum, epidermal growth factor, endothelial cell growth supplement and heparin) and 2% BSA was added to the wells for the times indicated in FIG. 3. After the indicated times, the wells were emptied and washed once with 1 ml of HBSS. 0.5 ml of HBSS with or without 1 IU/ml of heparinase I, II or III; or heparinases I and III were added to the wells. The plates were incubated at 37° C. on a heat block for 15 minutes with occasional agitation. After 15 minutes, the supernatants were collected and assayed for IL-8. An enzyme-linked immunosorbent assay (ELISA) system from Perseptive Diagnostics was used to determine IL-8 concentrations in the supernatants. The manufacturer's recommended protocol was followed. 90 ul of supernatant and 10 ul of 5M sodium chloride were used in each well of the ELISA plate. Each washing step utilized three repeats of 150 ul of washing solution per well, with 2-3 minutes of agitation between each repeat. The percent difference in the IL-8 concentration of supernatants from; IL-1b induced heparinase I, II or III treated endothelium, versus IL-1b induced non-treated endothelium are shown in FIG. 5. In addition, the IL-8 concentrations in the supernatants from IL-1b induced heparinase I, II or III treated endothelium are shown in FIG. 5.

Example 4

Treatment of Endothelial Cell Layers with Heparinase to Inhibit Neutrophil Adhesion In order to concentrate neutrophils at a site of inflammation, endothelial cell surface molecules activate rolling neutrophils for tight binding to the walls of postcapillary venules. Chemokines bound to heparin/heparan sulfate have been identified as important signal molecules for activation of neutrophils for tight binding in the microcapillaries. The in vitro neutrophil adhesion assay system described below is commonly used to analyze conditions affecting neutrophil adhesion to endothelial cells. Treatment of the activated human endothelial cell layers used in this assay with either heparinase I, II or III resulted in significant reductions in the level of neutrophil adhesion to the endothelium. These results demonstrate that heparinase treatment of the vasculature would inhibit localized neutrophil accumulation in the microcapillaries, and would inhibit inflammatory responses.

Isolation of Human Neutrophils 25 ml of venous blood was drawn from a healthy donor into 1/10 volume of 0.1M sodium citrate, pH 7.4, and was diluted with 25 ml of Dulbecco's phosphate-buffered saline containing calcium chloride and magnesium chloride (D-PBS). 10 ml aliquots of diluted blood were layered on 10 ml of Ficoll-Paque in 50 ml tubes. The tubes were centrifuged at 400×g for 30 minutes at 20° C., and were allowed to stop, without braking. The upper layers were removed and the pellets were resuspended in 3 volumes of a solution of 155 mM $NH_4Cl$, 10 mM $KHCO_3$ and 0.1 mM EDTA, pH 7.4 at 4° C., to lyse the erythrocytes. The tubes were inverted after a few minutes and the contents turn black after 7 to 8 minutes. After 10 minutes, the tubes were centrifuged again at 400×g for 5 minutes at 4° C. The supernatants were aspirated and the pellets were resuspended in the $NH_4Cl$ solution containing 0.5% human albumin. The suspensions were pooled and the volume was brought to 50 ml. The cell suspension was incubated on ice for 15 minutes and centrifuged at 400×g for 5 minutes at 4° C. The supernatant was removed and if the pellet was still red, it was washed again with $NH_4Cl$ solution containing 0.5% human albumin. Finally, the cells were resuspended in D-PBS with 5 mg/ml human albumin and refrigerated, until needed. A 10 μl aliquot of suspension was diluted with 10 μl of trypan blue and the cells were counted on a hemacytometer to determine the number of viable cells per volume of suspension.

Labeling of Neutrophils

A suspension of 10×106 neutrophils was made in 2 ml of PBS (no Ca, no Mg) with 5 mg/ml human albumin. BCECF-AM (Molecular Probes) was added to the suspension for a final concentration of 46 uM. The neutrophils were incubated in a water bath at a set temperature of 37° C. for 30 minutes after which they were centrifuged and rinsed twice with PBS (no Ca, no Mg) with 5 mg/ml human albumin. They were finally resuspended in 10 ml of RPMI+20% bovine fetal serum at 37° C.

Treatment of Endothelial Cells with Heparinases

HUVEC at passage number 3 were trypsinized and counted. The cells were plated in RPMI+20% bovine fetal serum+95 ug/ml heparin+ECGS+EGF at 5×104 cells per well in 96 well plates. They were grown at 37° C., 5% $CO_2$ for 18 hours. At that point the growth medium was replaced with RPMI+20% bovine fetal serum (2 ng/ml IL-1b for 4 hours. The cells were then rinsed with HBSS and treated with heparinase I, II or III at 0.1 IU/ml in HBSS for 1 hour at 37° C., 5% $CO_2$.

Neutrophil Adhesion Assay

After the treatment period, HUVEC were rinsed once with HBSS. 200 ul of the neutrophil suspension (which corresponds to 200,000 neutrophils) was added to each well of treated or control HUVEC. The plate was put at 37° C., 5% $CO_2$ for 30 minutes. The adhesion period was stopped by centrifuging the plate upside down at 250×g for 5 minutes. 200 ul of PBS (no Ca, no Mg)+5 mg/ml human albumin was added to each well and the plate was read with a Fluorolite 1000 fluorescence plate reader at a voltage of 2.5 V. The emission filter was a 535 nm±35 and the excitation filter at 485±22.

Analysis of Data

A standard curve was generated by putting known amounts of BCECF-AM-stained neutrophils, resuspended in PBS (no Ca, no Mg)+5 mg/ml human albumin in wells of another 96 well plate which contained confluent HUVEC layers. The fluorescence units were plotted against the quantity of neutrophils and a slope was calculated. The standard curve was used to determine the number of bound neutrophils in the control and heparinase treated wells. The percent differences between IL-1b activated HUVEC layers and comparable HUVEC layers treated with heparinases I, II and III are shown in FIG. 6.

Example 5

Treatment of Endothelial Cell Layers and Basement Membranes with Heparinase to Inhibit Neutrophil Extravasation Leukocytes from the blood accumulate in inflamed tissues by transmigration across the adjacent endothelium (extravasation). The endothelial cell layer is activated by the inflamed tissue (via cytokines and chemoattractants), and the affected endothelium directs and localizes the accumulation of leukocytes in the inflamed tissue. In order to activate leukocytes for extravasation, and to direct the migration of the leukocytes into the inflamed tissue, the activated endothelium forms an immobilized chemokine gradient on its cell surface and in its basement membrane. The in vitro neutrophil transmigration assay system described below is commonly used to analyze conditions affecting neutrophil extravasation. Treatment of the activated human endothelial cell layers used in this system with either heparinase I, II or III resulted in significant reductions in the level of neutrophil migration across the endothelium. These results demonstrate that heparinase treatment of the vasculature would inhibit localized neutrophil accumulation and inflammatory responses.

Assay of Neutrophil Extravasation

Neutrophils were isolated as described in example 4. Human fibronectin was dissolved at 0.4 mg/ml in RPMI medium without serum. Filter inserts (6.25 mm) of pore size 3 μm or 8 μm, were coated with 4 μg/cm2 of human fibronectin one hour at room temperature, and were rinsed with distilled water. Wells of a 24 well plate were filled with 0.3 ml of RPMI medium with 20% fetal bovine serum, 95 μg/ml heparin, 200 μg/ml ECGS and 10 ng/ml EGF. The coated filter inserts were seated in the wells, and 8×104 human umbilical venous endothelial cells (HUVEC; used at passages 1 to 7) in 0.3 ml of complete RPMI medium, were plated on the coated filter inserts. The cells were allowed to grow for 48 to 65 hours, at 37° C., in 5% $CO_2$. The culture medium from the filter inserts and the wells was changed once during the growth period for RPMI medium lacking heparin. After the growth period, the culture medium underneath all inserts, except negative control inserts, was removed and replaced with fresh culture medium lacking heparin and growth factors, but containing 2 ng/ml of human recombinant IL-1b. The culture medium under negative control inserts was replaced with fresh culture medium. The multiwell plates were incubated at 37° C., in 5% $CO_2$, for 4 hours. The medium was removed from the inserts and wells and the cells were rinsed once with Hank's Balanced Salt Solution (HBSS). The filters and wells were filled with 0.3 ml of a solution of HBSS; treated inserts received HBSS containing heparinase I, II or III instead of HBSS. This treatment was performed for the times indicated in FIG. 1, at 37° C., in 5% $CO_2$. The solution was removed and the cells were rinsed once with HBSS. 0.3 ml of fresh culture medium without heparin and growth factors was added to the wells and 1.5×106 of freshly prepared human neutrophils in 0.3 ml of culture medium without heparin and growth factors were added to all of the inserts. The plates were incubated at 37° C., in 5% $CO_2$, for the times indicated in FIG. 3. After this time, the inserts were removed and the bottoms were rinsed once with 0.3 ml D-PBS. The contents of the well were removed and the well was washed with 0.3 ml of D-PBS. The rinses were added to the well contents and the combined contents were brought to a 1 ml volume. These samples were frozen for up to 16 hours before assaying for myeloperoxidase activity.

Myeloperoxidase Assay

Standards containing between 1×105 and 1×106 neutrophils in a 1 ml volume were produced by diluting an aliquot of the neutrophil suspension in D-PBS. 4 ml of 5 mM potassium phosphate, pH 6.7, containing 0.5% hexadecyltrimethylammonium bromide and 0.5% triton was added to each standard and thawed sample. 0.1 ml of each sample or standard was added to a plastic cuvette. 2.9 ml of 50 mM phosphate buffer, pH 6.0 containing 0.167 mg/ml o-dianisidine hydrochloride and 0.0005% hydrogen peroxide were added to the cuvettes. The change in absorbance at 460 nm was monitored every 30 seconds for 3 minutes by use of a spectrophotometer.

The rate changes obtained from the standards were used to produce a curve of the rate of increase in absorbance versus numbers of neutrophils. This curve was used to quantitate the number of neutrophils in each sample, which had migrated through, either a treated, or an untreated endothelial layer. The number of migrating neutrophils was divided by 1.5×106 to determine the percentage of neutrophil migration.

Analysis of Data

The effectiveness of the heparinase treatment in this assay depended on the extent to which the HUVEC were covering the filter surface. The extent of coverage was based on dye exclusion analysis performed after an extravasation experiment, and it varied somewhat from filter to filter in a single experiment. Generally, if the filter was densely covered with a tightly packed HUVEC layer, the percentage of extravasating neutrophils was low (<10%), and the differences between treated and untreated wells were not statistically significant (large well to well variability). If large areas of the filter were not covered with a HUVEC layer (estimated at 30-40% of the filter) large numbers of neutrophils (40-60%) would migrate through the filter, but a 1 hour heparinase treatment would not be as effective in inhibiting the migration. This migration is not comparable to extravasation, which can be functionally defined as neutrophils squeezing between neighboring endothelial cells. If 75 to 90% of the filter was covered with HUVEC, generally, 15 to 30% of the neutrophils extravasated, and the 1 hour heparinase treatment was found to be most effective under these conditions.

Figure 7:
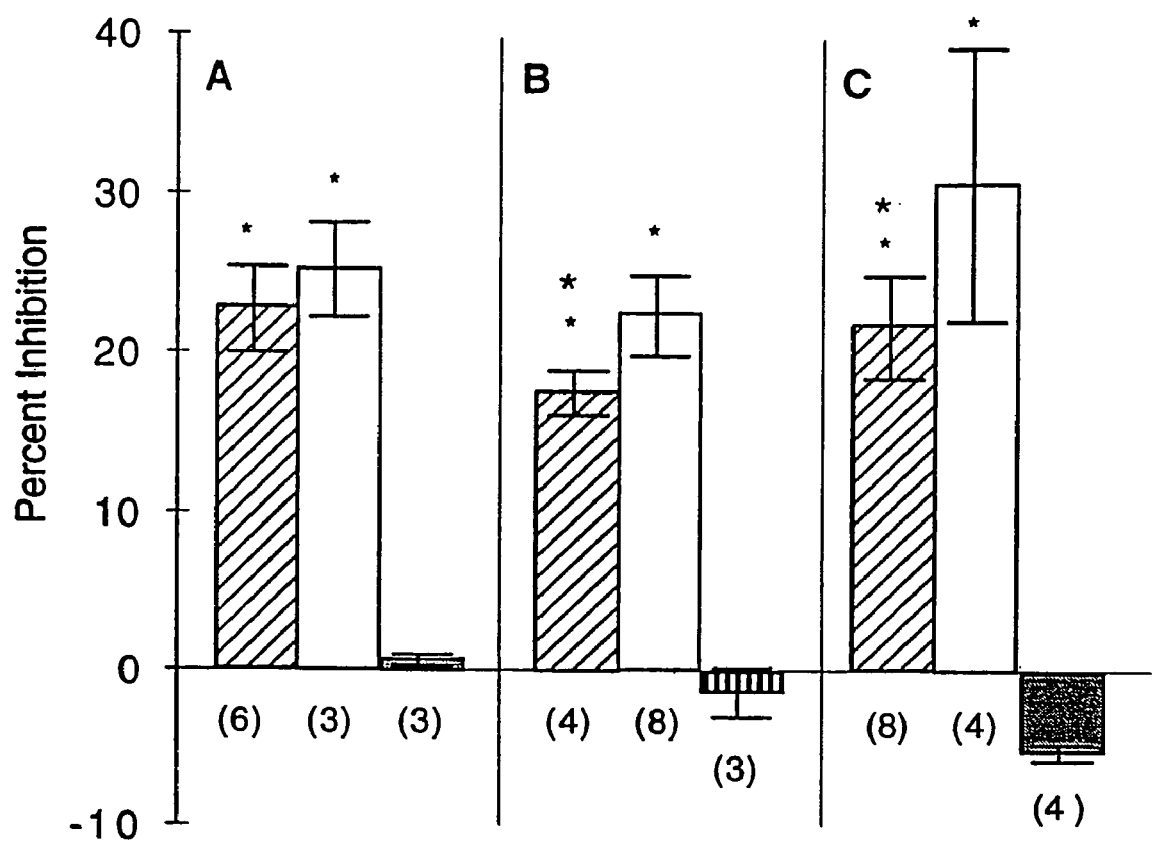

Using the Student's t-test, experiments were analyzed to determine if a significant effect for the 1 hr heparinase treatments had been observed (P<0.05). The data from these experiments was combined and is displayed in FIG. 7. The data for the 15 minute heparinase treatments shown in FIG. 7 is derived from the same experiments as the 1 hour treatments. The Student-Newman-Keuls test was used to determine the significance of the differences (P<0.05) between different treatments with the same enzyme. Significant differences are indicated by asterisks (*) in FIG. 7.

Example 6

Treatment of Endothelial Cell Layers and Basement Membranes with Human Heparinase (b-Thromboglobulin) to Inhibit Neutrophil Extravasation Commercial preparations of b-thromboglobulin are a mixture of the chemokines CTAP-III and NAP-2. At non-physiological pH (pH 5.8-6), these chemokines have heparinase activity, while at pH 7, they bind heparin and act as chemotactic cytokines for leukocytes. The heparinase activity of commercial b-thromboglobulin preparations were analyzed at pH 5.8 and pH 7, by digestion of radioactive $35SO_4$-labeled ECM. These preparations showed significant human heparinase activity only at pH 5.8. They were then used in the in vitro extravasation assay system described in example 5, in order to determine if the human heparinase activity could prevent extravasation of neutrophils across an endothelial cell layer. The treatment of activated human endothelial cell layers with human heparinase (b-thromboglobulin) resulted in a significant reduction in neutrophil extravasation. These results demonstrate that heparinase treatment of the vasculature with human heparinase would inhibit localized neutrophil accumulation and inflammatory responses.

Activity of b-thromboglobulin on Labeled Matrix

Commercial b-thromboglobulin was tested for heparinase activity at pH 5.8 and pH 7 by release of $35SO_4$-labeled heparin/heparan sulfate from ECM. Bovine corneal endothelial cells at passage 1 to 8 were split 1:10 form a confluent plate and seeded in 4 well plates in DMEM low glucose with 10% fetal bovine serum, 5% calf serum and 4% Dextran added. The dishes received 1 ng/ml bFGF 3 times a week prior to reaching confluency. Just prior to reaching confluency, $Na_2{}^{35}SO_4$ in $H_2O$ diluted to 1 mCi/ml with DMEM low glucose was added to the cells at a final concentration of 25 uCi/ml, in Fisher medium with 10% fetal bovine serum, 5% calf serum and 4% Dextran. 3 to 4 days later, the label was given again. The plates were left undisturbed 12 to 14 days post confluency. To harvest the matrix, the medium was removed and replaced with a solution of 0.5% Triton, 0.02M $NH_4OH$ in PBS (no Ca, no Mg). This solution was removed and the matrix was washed 3 times with PBS (no Ca, no Mg). The plates were stored, at 4° C., covered with PBS. These matrices were used within a year.

b-thromboglobulin from Wellmark (product #41705) or Calbiochem (product #605165) were used for digestion of the labeled ECM. 100 ug of enzyme was dissolved in 1 ml of water (Wellmark) or PBS (Calbiochem). A further dilution was done in PBS at pH 5.8 or 7. The matrices were covered with 250 ul of PBS alone or PBS with 1 or 5 ug of β-thromboglobulin. The matrices were incubated in a $CO_2$ incubator for 3 hours. Aliquots of 100 ul were taken from every well and counted. The amount of radioactivity released from each enzyme-treated matrix was compared to an untreated matrix, and the results are displayed in FIG. 8.

Migration of Neutrophils across HUVEC Treated with β-thromboglobulin

HUVEC were grown on filter inserts and activated as described in example 5. Five ug of β-thromboglobulin in PBS at pH 5.8 or PBS alone were applied to the HUVEC layer for one hour. Neutrophils were added above the filters and the number of extravasating neutrophils were quantitated as described in example 5. The effect of the human heparinase treatments on neutrophil extravasation are shown in FIG. 9.

Example 7

Treatment of Rats with Heparinase Inhibits Leukocyte-Endothelial Cell Interactions Following Ischemia/Reperfusion This example illustrates the effect of heparinase III on leukocyte behavior in vivo. Three key mechanisms of leukocyte accumulation in inflamed tissues; leukocyte rolling, sticking, and extravasation, were analyzed in rat skeletal muscle microvasculature following ischemia. Pretreating the vasculature with heparinase III prior to ischemia, and maintaining the plasma concentration of heparinase III constant during reperfusion was found to significantly decrease leukocyte rolling, sticking and extravasation. This example demonstrates that heparinase treatment of vasculature would inhibit neutrophil accumulation in microcapillaries and in the surrounding tissues. In vivo heparinase treatment would result in deceased inflammatory responses. As also demonstrated by this example, heparinase treatment significantly increased microvascular perfusion within reperfused muscle following ischemia. In addition to decreased neutrophil accumulation, increased microvascular perfusion would positively affect the recovery of muscle tissue and positively affect the outcome of ischemia/reperfusion (i.e. inflammatory) events.

General Comments

In order to establish a plasma level of approximately 1 IU/ml, we undertook pilot studies to test the effect of infusing Heparinase over the 5 hour period of time required for our in vivo studies. A previous publication on the leukocyte behavior following 3 hr ischemia (Forbes et al., 1996, Microvascular Research 51:275-287) contains data on naive and sham treated rats. Because the methods and timing were the same for this previous study and the present study of 3 hr ischemia, the effect of heparinase treatment will be compared to the naive and sham results obtained from the previously published results. For the 2 hr ischemia protocol, additional naive and sham treated rats were analyzed.

In order to investigate directly the effect of heparinase, in vivo, we applied intravital video microscopy to the extensor digitorum longus muscle in the rat hind limb. This analysis occurred during a period of 105 or 90 minutes of reperfusion, which followed 2 or 3 hours, respectively, of no-flow ischemia. Such periods of ischemia/reperfusion (I-R) result in an inflammatory response in skeletal muscle sufficient to cause increased leukocyte-endothelial cell interactions.

Methods

Male Wistar rats weighing 225 to 250 gm were anesthetized by inhalation of halothane (1%-1.5%) and the carotid artery and jugular vein cannulated to monitor blood pressure and permit infusion of fluids, respectively. The extensor digitorum longus (EDL) muscle in the rat hind limb was prepared for intravital microscopy. Briefly, with the anaesthetized rat lying on the stage of the microscope, the EDL muscle was exposed by reflection of the overlying skin and separation of the tibialis anterior and gastrocnemius muscles. A suture was tied around the distal tendon of the muscle allowing reflection of the overlying skin and saline bath positioned on the microscope stage. Normal muscle and body temperatures were maintained (i.e., muscle at 32° C. body at 37° C.) by heat lamps. The muscle was covered by a glass cover slip and all exposed tissue covered with Saran wrap to prevent dehydration. Following the preparation of the EDL muscle for intravital video microscopy, and a 30 minute period of recovery, to allow microvascular blood flow to return to normal following the hyperaemia induced by the preparatory methods, 1-2 fields of view each containing two or more postcapillary venules were chosen. These fields of view were used throughout the experiment so that temporal changes in leukocyte flow behavior could be measured. One minute recordings of these fields of view were made using low magnification to provide information regarding RBC flow within individual capillaries. Following the low magnification recordings, views of the postcapillary venules were recorded for 1 min at high magnification. The video recording of such views allows for the "off-line" analysis of microcirculatory parameters. Thus, control values of the density of perfused capillaries and the flow behavior of leukocytes (number of stuck, rolling and extravasating per unit area) were measured.

Plasma levels of heparinase III are measured using a heparinase III ELISA. The heparinase III ELISA is a quantitative two-antibody sandwich assay. Affinity purified anti-heparinase III rabbit antibodies are coated onto a microtiter plate. Wells are washed and incubated for 2 hours at 37° C. with blocking buffer (TBS, 1% BSA+1% Tween 20). After 3 washes, standards and samples are added to the wells and any heparinase III present is bound by the immobilized antibody. Any unbound substance is then washed away and biotin labeled anti-heparinase III rabbit antibodies are added to the wells. Excess antibodies are removed by washing. Peroxidase-conjugated streptavidin is added and binds to any biotin complex present in the well. After washing away any unreacted streptavidin, a substrate solution containing hydrogen peroxide and 3,3',5,5' tetramethylbenzidine in aqueous DMF is added to the wells, according to the procedure described for the TMB Peroxidase EIA Substrate Kit (Biorad, CA), and color develops in proportion to the amount of heparinase III in the sample. A 1 N $H_2SO_4$ solution stops the reaction and the absorbance is measure at 450 nm.

Specific Protocol

A series of rats were infused with heparinase III via the venous catheter at a rate of 3 ml/hr for 5 hr. to maintain a heparinase level of 1.0 IU/ml in the blood. Through such pilot studies it was determined that 0.33 IU/gm body weight/hr was adequate for this purpose.

Microvascular blood flow and leukocyte behavior was recorded every 15 min for a total of 90 to 105 min of reperfusion. Blood samples were taken before the administration of heparinase and during reperfusion to ensure correct plasma concentrations of heparinase.

Statistical Analysis

In all cases means are expressed with their standard error of estimate. Comparisons were made using analysis of variance (ANOVA) followed where appropriate by Scheffé tests as ad hoc analysis. Significance was assumed at $p > 0.05$.

Results

A plasma concentration of approximately 1 IU/ml (adjusted for activity) was achieved during infusion, and in spite of a trend toward increased plasma levels during the last 2 hours of infusion, the plasma concentration remained constant (FIG. 10). Prolonged infusion of heparinase III appeared to have no adverse side-effects at least in terms of blood pressure, or rate of respiration.

Immediately following 3 hr of ischemia, the number of rolling leukocytes (Lr) significantly increased in sham I-R rats (14.77±1.33), compared to naive (no I-R) rats (5.66±0.11). The average number of rolling leukocytes remained constant at these levels during reperfusion in both the sham and naive rats for the duration of the 90 minute reperfusion period (FIG. 3). In spite of 3 hr ischemia, no change in leukocyte rolling within postcapillary venules of heparinase III treated rats was measured. In fact, the average number of rolling leukocytes following heparinase treatment (2.81±0.64) tended to be less than in naive rats over the 90 minute observation period (FIG. 11).

The number of leukocytes stuck to the wall of postcapillary venules (Ls) progressively increased in sham I-R rats, reaching a constant level (11.96±0.01) within 45 minutes of the release of the tourniquet (3 hr ischemia). However, the number of stuck leukocytes in heparinase III treated rats showed no change following ischemia, and was not significantly different from naive rats (FIG. 12).

As would be expected based on the low numbers of sticking leukocytes following heparinase III treatment, the number of extravasated leukocytes (Le) did not change during reperfusion after 3 hr of ischemia (FIG. 13). Le for sham and naive rats are not available for the 3 hr ischemia protocol. For a 2 hr ischemia protocol, the Le for the heparinase III treated rats was higher than for the naive rats, but was significantly lower than the Le in the sham treated animals. This data is displayed in FIG. 14, as the percent difference in the Le for heparinase and sham treated rats vs. naive rats.

Following release of the tourniquet after 3 hr of ischemia, a significant decline in microvascular perfusion (CDper) occurred in both the sham and heparinase III treated rats, compared to perfusion measured in naive rats. However, unlike the perfusion in sham rats microvascular perfusion in heparinase III treated muscles returned to normal within 30 minutes of the release of the tourniquet (FIG. 15).

Example 8

Cardioprotective Effects of Heparinase III in a Rabbit Preparation of Ischemia/Reperfusion Injury Introduction Ischemia produces a significant degree of damage at the level of myocytes and endothelial cells within the coronary vascular bed; this can lead to extravasation of plasma and other blood and cellular components into the interstitial space. Polymorphonuclear leukocytes can migrate through the endothelial cell layer; this migration of neutrophils across the connective tissue barrier is dependent on the actions of neutrophil-derived proteolytic enzymes even in the presence of plasma antiproteases. Restoration of blood flow allows rapid access of inflammatory cells to jeopardized myocardium. Neutrophil adhesion to endothelial cells is stimulated by endotoxin IL-1b (activates vascular endothelium to produce adherence molecules for leukocytes) or tumor necrosis factor. A number of studies have explored the possibility of using various-pharmacologic interventions including monoclonal antibodies to prevent neutrophil adhesion to vascular or myocardial-cells particularly during the reperfusion phase. Interfering with neutrophil-cellular interactions (neutrophil rolling, adhesion and extravasation) has been shown to significantly reduce the extent of cellular injury following ischemia-reperfusion. This suggests that inflammatory cells play an important role in the pathophysiology of ischemia-induced cellular injury; inflammatory cells may also play a role in extending myocyte injury beyond that which occurs during the ischemic insult (i.e., reperfusion injury). Because heparinase treatment is effective for inhibition of neutrophil-endothelium interactions (see examples above), prevention of reperfusion injury to rabbit myocardium by treatment with heparinase was investigated in the experiments described in this example. Heparinase III was found to attenuate the extent of tissue necrosis when administered at a target dose of 25 ug/ml either before the onset of coronary occlusion or at the onset of reperfusion. Lower dosages of heparinase III did not provide cardioprotection in this animal preparation of ischemia-reperfusion injury; however, at a target dose of 5 ug/ml there was a trend toward reduced infarct size. Protection was obtained without significant changes in cardiac hemodynamics or transmural blood flow distribution.

When an inflammatory response is the result of an ischemic episode as in the non-limiting examples of heart attack and stroke, this example demonstrates that heparinase treatment before or at the time of the inflammatory event can reduce tissue injury. In addition, this example indicates that tissue damage resulting from leukocyte accumulation during any inflammatory event can be reduced by heparinase treatment or pretreatment.

Methods

Male New Zealand White rabbits (2.2-3.0 Kg body weight) were used for these studies. Rabbits were cared for in accordance with the *Guide to the Care and Use of Experimental Animals* (vol. 1 and 2) of the Canadian Council on Animal Care. They were premedicated with intramuscular acepromazine maleate (5 mg/Kg; Austin Laboratories) and anesthetized with pentobarbital sodium (25 mg/Kg; i.v.; MTC Pharmaceuticals). Additional anesthetic was administered hourly. The trachea was cannulated and rabbits were mechanically ventilated with room air. The right jugular vein was cannulated for administration of drugs (Heparinase III or vehicle); the left jugular vein was cannulated to permit withdrawal of blood for determinations of plasma heparinase levels. A cannula (PE-90) was placed in the left carotid artery for withdrawal of reference arterial blood during injection of radiolabeled microspheres.

The heart was exposed via a left thoracotomy and a snare (4-0 silk) placed around the first anterolateral branch of the left circumflex coronary artery midway between the atrioventricular groove and the apex. The silk suture was passed through a length of Tygon tubing to provide a snare for coronary occlusion. Left ventricular chamber pressure was obtained with a fluid-filled catheter positioned via the apex. Cardiac hemodynamics were allowed to stabilize for 20 minutes.

Regional myocardial ischemia was induced by pulling the suture through the plastic tubing and clamping with a mosquito hemostat. Ischemia was verified visually by the appearance of regional epicardial cyanosis and ST segment elevation on the electrocardiogram (Lead II). In hearts that developed ventricular fibrillation normal sinus rhythm was restored by gentle flicking of the LV (electrical cardioversion was not used in these experiments); hearts that could not be cardioverted after two attempts were excluded from the data analysis. Lead II electrocardiogram and LV pressure were recorded throughout the experiments with a Gould (TA240) EasyGraph 4-channel physiograph recorder (Interfax Inc., Montreal, Quebec).

Experimental Protocol

Rabbits were assigned to seven different treatment groups; Group 1 rabbits were given saline (i.v.) for 60 minutes prior to onset of ischemia; Group 2 rabbits were given saline (i.v.) at the onset of coronary reperfusion; Group 3 rabbits were given heparinase III (25 ug/ml target level, i.v.) for 60 minutes prior to onset of ischemia; Group 4 rabbits were given heparinase III (25 ug/ml target level, i.v.) at the onset of coronary reperfusion; Groups 5, 6 and 7 rabbits were given target levels of either 0.25, 1.25, or 5.0 (g/ml heparinase III, respectively at the onset of coronary reperfusion. Drug or saline was infused intravenously (4.0 ml/hr) for 60 minutes prior to onset of myocardial ischemia in two treatment groups (Groups 1 and 3) and then continuously for 2 hours using a Harvard infusion PUMP (Ealing Scientific, Montreal, Canada). In the remaining experimental groups vehicle or drug infusion was initiated at the time of reperfusion and continued for 3 hours during reperfusion. Rabbits were assigned to a particular group by rotating drug treatment on succeeding experiments through the seven treatment protocols. All rabbits were subjected to 45 minutes of regional coronary occlusion followed by 180 minutes of reperfusion.

Plasma Heparinase III Determinations

Blood samples were obtained from the right jugular vein at baseline, 30 and 60 minutes after vehicle or drug infusion in Group 1 and 3 rabbits; blood was also obtained at 15, 30, 60, 120 and 180 minutes of coronary reperfusion. In the remaining experimental groups blood was obtained at baseline and 15, 30, 60, 120 and 180 minutes of coronary reperfusion. Blood samples were centrifuged for 15 minutes at 1500 rpm at 4° C.; plasma was frozen and stored at −20° C. for later analysis. Heparinase III plasma levels were determined as described in example 7. Transmural Blood Flow Blood flow to ischemic and non-ischemic vascular beds was measured using radiolabeled microspheres (±15 um; NEN, Boston, Mass.) using the reference withdrawal technique. For each blood flow measurement, 0.4-0.6×106 microspheres labeled with either 113Sn, 46Sc, or 85Sr (agitated mechanically with a vortex mixer immediately before use) were injected into the left atrium under hemodynamic steady-state conditions followed by two flushes with 3 ml warmed saline (injection of microspheres into the left atrium ensures adequate mixing in the LV chamber and prevents streaming artifacts which occur with direct injections of microspheres into the coronary circulation). Reference arterial blood samples from the carotid artery were collected beginning 10 seconds before the injection of microspheres and continuing for 2 minutes thereafter at a rate of 2.6 ml/min. Myocardial blood flow distribution was assessed at; 1-baseline, 2-30 minutes after onset of coronary reperfusion and 3-180 minutes coronary reperfusion. Tissue and reference blood radioactivity is measured using a multichannel pulse-height analyzer (Cobra II, Canberra Packard) with correction for overlap of isotope spectra.

Analysis of Infarct Size

At the end of the experimental protocol, hearts were arrested in diastole by intravenous injection of 10 ml of saturated potassium chloride, quickly extirpated, rinsed in saline and cannulated via the aorta on a Langendorff perfusion apparatus. Hearts were perfused ex vivo via the aorta at 75 mm Hg with 2,3,5-triphenyltetrazolium chloride at 37° C. for 20 minutes. Subsequently, the arterial suture was re-tied and Monastral Blue was injected retrogradely via the aortic cannula to allow delineation of the anatomic risk zone. Hearts were then removed from the perfusion apparatus, the atria and right ventricle were trimmed away, and the left ventricle was weighed and fixed by immersion in buffered 10% formalin.

Post-Mortem Studies

The principal end-point of this study was the effect of drug treatment on infarct size (normalized to anatomic risk zone size), assessed using tetrazolium staining. Hearts were sectioned into 2 mm slices and the outline of the LV slices and the tetrazolium-negative (i.e., infarct) areas were traced onto clear acetate sheets. Anatomic risk zone was delineated by the absence of Monastral blue dye and traced onto dear acetate sheets. Infarcts were normalized to anatomic risk zone size for each heart. Total LV cross-sectional area, risk area, infarct area were determined from enlarged tracings (1.5×) by computerized planimetry (Sigma Scan; Jandel Scientific Inc., Calif.) using a Summagraphics Summasketch Plus Bitpad connected to an IBM PS/2 computer. Risk volume, infarct volume, and LV volume for each slice was calculated as the sum of the area obtained by computerized planimetry and the thickness of each ventricular slice. The values from the sequential slices were summed to provide the total volume of the LV, risk zone and infarct zone.

Data Analysis

Differences in hemodynamic data before and after coronary occlusion were examined using one-way ANOVA. Heart rate-blood pressure product was used as an index for cardiac metabolic demand. Infarct volume, risk volume, infarct size, and LV volume were compared by a one-way. ANOVA Where overall group differences were detected, Dunnett's multiple comparison test was used for comparison to controls. All statistical comparisons were made with Statistical Analysis Systems Programs (SAS Insitute, Cary, N.C.) for the personal computer. A probability (p) level of less than 0.05 was considered statistically significant. To establish sample size for this study, "n/group" values were calculated to provide a 0.90 power to detect a minimum 15 percent reduction (expected standard deviation of 8%) of infarct size.

Results

One hundred thirty rabbits were entered into the present studies; five rabbits died due to respiratory failure (n=1), surgical error (n=1), or non-convertible ventricular fibrillation (n=3). Thirty-six rabbits were included in the dose-response studies and another 28 were assigned to the biochemical evaluations (cardiac hemodynamic and plasma heparinase III levels were included in the overall statistical analysis). Consequently, sixty-one rabbits were included in the infarct size data analyses.

Cardiac hemodynamic variables are summarized in Table 1. Heart rate, left ventricular systolic and diastolic pressures and heart rate-blood pressure product (indicator of myocardial oxygen demand) before the onset of coronary occlusion is were comparable for all of the treatment groups. Heart rate-blood pressure product (FIG. 16) appeared to be higher at 60 minutes reperfusion in rabbits treated with heparinase III (25 ug/ml target level) at the time of reperfusion (Group 4); however, cardiac hemodynamics were similar for all animals at the end of the study.

Data on left ventricular weight, infarct and risk volume, infarct size and anatomic risk area as percent of LV volume are summarized in Table 3. Infarct size (FIG. 17), normalized to risk zone size, was 42.3±4.8 (mean±1 SD) and 40.0±5.3 percent (p=NS) in controls with/without vehicle pre-treatment, respectively. Heparinase III pretreatment and heparinase III given at the time of reperfusion at the 25 ug/ml target level resulted in a significant reduction (p=0.01 versus vehicle treated controls) in myocyte necrosis of 26.1±5.2 and 24.7±5.1 percent, respectively; no differences were detectable between groups treated either pre-ischemia or at the time of coronary reperfusion. Treatment with heparinase III at 0.25, 1.25 or 5.0 ug/ml target levels did not limit infarct size; they were 42.8±6.5, 39.1±5.4 and 37.9±4.6 percent respectively. There was a slight trend to smaller infarcts in the 5.0 (g/ml treatment group with p value of 0.666.

Heparinase III injectate levels which were administered to the respective treatment groups are shown in FIG. 18. The initial heparinase III target dose (i.e., therapeutic dose) of 25 ug/ml was investigated followed by the respective drug dilutions of 1:5, 1:20 and 1:100; dilutions were made with saline. A time-course of actual plasma heparinase III concentrations is shown in FIG. 19; pre-treatment with heparinase III and treatment at the time of reperfusion provided similar plasma drug concentrations in Groups 3 and 4. Plasma heparinase III concentrations were considerably lower after 3 hours coronary reperfusion in rabbits which were initially pre-treated (drug only administered during first 3 hours of experimental protocol); most importantly, the drug was on board at the time of coronary reperfusion. This may account for the similar results obtained in Groups 3 and 4 with respect to infarct size.

TABLE 1

Summary of Cardiac Hemodynamics

| Group | HR (bpm) | LVPsys (mm HG) | LVPdias (mm HG) | RPP (mm Hg × bpm) |
|---|---|---|---|---|
| Baseline | | | | |
| 1 | 229 ± 34 | 63 ± 8 | 2 ± 1 | 14,192 ± 3,643 |
| 2 | 245 ± 31 | 58 ± 10 | 2 ± 2 | 13,705 ± 2,739 |
| 3 | 246 ± 29 | 64 ± 10 | 3 ± 3 | 15,169 ± 3,629 |
| 4 | 242 ± 39 | 70 ± 12 | 3 ± 2 | 16,276 ± 4,180 |
| 5 | 254 ± 27 | 67 ± 11 | 2 ± 2 | 16,432 ± 2,718 |
| 6 | 231 ± 34 | 63 ± 12 | 1 ± 1 | 14,389 ± 4,116 |
| 7 | 233 ± 28 | 67 ± 12 | 1 ± 1 | 15,293 ± 3,757 |

TABLE 1-continued

Summary of Cardiac Hemodynamics

| Group | HR (bpm) | LVPsys (mm HG) | LVPdias (mm HG) | RPP (mm Hg × bpm) |
|---|---|---|---|---|
| Ischemia (30 minutes) | | | | |
| 1 | 218 ± 26 | 57 ± 8 | 4 ± 3 | 11,518 ± 2,904 |
| 2 | 237 ± 33 | 49 ± 11 | 4 ± 3 | 10,833 ± 3,372 |
| 3 | 241 ± 29 | 60 ± 8 | 6 ± 4 | 11,586 ± 2,634 |
| 4 | 236 ± 40 | 64 ± 11 | 5 ± 4 | 14,216 ± 3,832 |
| 5 | 228 ± 31 | 61 ± 12 | 2 ± 2 | 13,421 ± 3,545 |
| 6 | 219 ± 34 | 60 ± 13 | 4 ± 3 | 12,639 ± 4,551 |
| 7 | 211 ± 26 | 58 ± 8 | 4 ± 2 | 11,434 ± 2,704 |
| Reperfusion (30 minutes) | | | | |
| 1 | 206 ± 41 | 57 ± 8 | 3 ± 2 | 11,257 ± 3,731 |
| 2 | 229 ± 43 | 50 ± 9 | 3 ± 2 | 11,006 ± 3,755 |
| 3 | 201 ± 32 | 60 ± 10 | 5 ± 3 | 11,129 ± 3,069 |
| 4 | 238 ± 33 | 64 ± 11 | 5 ± 3 | 14,218 ± 4,031 |
| 5 | 206 ± 24 | 61 ± 11 | 3 ± 3 | 12,166 ± 2,833 |
| 6 | 197 ± 32 | 59 ± 11 | 2 ± 1 | 11,523 ± 3,825 |
| 7 | 191 ± 22 | 57 ± 11 | 3 ± 2 | 10,447 ± 2,888 |
| Reperfusion (60 minutes) | | | | |
| 1 | 199 ± 26 | 57 ± 7 | 3 ± 2 | 10,921 ± 2,695 |
| 2 | 220 ± 42 | 52 ± 10 | 3 ± 2 | 11,022 ± 3,932 |
| 3 | 197 ± 28 | 61 ± 13 | 5 ± 3 | 11,038 ± 2,981 |
| 4 | 233 ± 34 | 67 ± 12 | 5 ± 3 | 14,313 ± 4,082 |
| 5 | 199 ± 27 | 60 ± 11 | 2 ± 2 | 11,467 ± 3,172 |
| 6 | 182 ± 31 | 59 ± 11 | 2 ± 2 | 10,416 ± 3,151 |
| 7 | 183 ± 22 | 59 ± 10 | 4 ± 3 | 10,091 ± 2,138 |
| Reperfusion (120 minutes) | | | | |
| 1 | 177 ± 22 | 57 ± 8 | 2 ± 1 | 9,701 ± 2,499 |
| 2 | 197 ± 40 | 52 ± 10 | 3 ± 2 | 9,745 ± 3,870 |
| 3 | 188 ± 29 | 62 ± 12 | 5 ± 3 | 10,736 ± 3,180 |
| 4 | 210 ± 37 | 65 ± 13 | 6 ± 4 | 14,313 ± 4,082 |
| 5 | 184 ± 31 | 61 ± 13 | 2 ± 2 | 10,967 ± 3,624 |
| 6 | 165 ± 26 | 59 ± 11 | 2 ± 2 | 9,366 ± 2,587 |
| 7 | 165 ± 21 | 56 ± 10 | 3 ± 3 | 8,926 ± 2,164 |
| Reperfusion (180 minutes) | | | | |
| 1 | 156 ± 32 | 53 ± 13 | 2 ± 1 | 8,188 ± 3,450 |
| 2 | 187 ± 46 | 49 ± 5 | 4 ± 3 | 8,482 ± 2,163 |
| 3 | 178 ± 36 | 58 ± 10 | 4 ± 2 | 9,573 ± 2,591 |
| 4 | 206 ± 40 | 65 ± 15 | 7 ± 4 | 11,924 ± 4,116 |
| 5 | 172 ± 35 | 58 ± 12 | 2 ± 2 | 9,899 ± 3,542 |
| 6 | 154 ± 28 | 59 ± 12 | 2 ± 2 | 9,123 ± 3,313 |
| 7 | 154 ± 22 | 55 ± 10 | 2 ± 2 | 8,162 ± 2,346 |

Values are means ±1 SD.

HR = heart rate;

LVPsys = systolic left ventricular chamber pressure;

LVPdias = diastolic left ventricular chamber pressure;

RPP = heart rate-blood pressure product.

TABLE 2

Myocardial Blood Flow in Ischemic and Non-ischemic Perfusion Beds

| Group | Ischemic perfusion bed | | | Non-ischemic perfusion bed | | |
|---|---|---|---|---|---|---|
| | BASE | 30" RP | 180" RP | BASE | 30" RP | 180" RP |
| 1 | 2.17 ± 0.99 | 1.90 ± 0.57 | 1.02 ± 0.63 | 1.91 ± 1.11 | 2.20 ± 0.78 | 1.22 ± 0.64 |
| 2 | 2.73 ± 1.31 | 1.64 ± 0.75 | 0.88 ± 0.32 | 2.52 ± 1.07 | 1.92 ± 0.71 | 1.38 ± 0.23 |
| 3 | 2.13 ± 1.11 | 1.24 ± 0.711 | 1.17 ± 0.96 | 2.38 ± 0.78 | 1.78 ± 0.51 | 1.71 ± 0.69 |
| 4 | 2.33 ± 0.83 | 1.68 ± 0.87 | 0.84 ± 0.47 | 2.52 ± 0.71 | 2.24 ± 0.64 | 1.42 ± 0.46 |
| 5 | 2.76 ± 1.15 | 1.98 ± 0.65 | 1.27 ± 0.55 | 2.74 ± 1.55 | 1.83 ± 0.55 | 1.36 ± 0.28 |
| 6 | 2.43 ± 0.70 | 2.41 ± 0.38 | 1.57 ± 0.58 | 2.19 ± 0.68 | 2.24 ± 0.36 | 1.46 ± 0.29 |
| 7 | 2.38 ± 0.45 | 2.14 ± 0.76 | 1.13 ± 0.49 | 2.41 ± 0.58 | 2.20 ± 0.61 | 1.39 ± 0.35 |

Values are means ±1 SD. 1p(0.05 versus Group 6.
BASE = baseline flow measurement (i.e., before ischemia);
RP = coronary reperfusion. Data are expressed in ml/min/g wet weight.

TABLE 3

Infarct Size Measurements

| Group | n | Htwt (g) | AN (cm3) | AR (cm3) | ANAR (%) | ARLV (%) |
|---|---|---|---|---|---|---|
| 1 | 9 | 4.46 ± 0.28 | 0.51 ± 0.11 | 1.22 ± 0.27 | 42.3 ± 4.8 | 36.5 ± 6.7 |
| 2 | 9 | 4.53 ± 0.63 | 0.41 ± 0.07 | 1.04 ± 0.18 | 40.0 ± 5.3 | 33.9 ± 5.8 |
| 3 | 9 | 4.71 ± 0.69 | 0.26 ± 0.06$^1$ | 1.03 ± 0.31 | 26.2 ± 4.9$^1$ | 33.3 ± 8.1 |
| 4 | 9 | 4.51 ± 0.77 | 0.24 ± 0.07$^1$ | 0.98 ± 0.24 | 24.7 ± 5.1$^1$ | 31.7 ± 7.2 |
| 5 | 8 | 4.30 ± 0.52 | 0.36 ± 0.12 | 0.91 ± 0.12 | 42.8 ± 6.5 | 29.4 ± 4.6 |
| 6 | 9 | 4.61 ± 0.52 | 0.39 ± 0.08 | 1.02 ± 0.27 | 39.1 ± 5.4 | 32.0 ± 7.9 |
| 7 | 9 | 4.02 ± 0.63 | 0.30 ± 0.05 | 0.80 ± 0.18$^1$ | 37.9 ± 4.6 | 27.5 ± 6.7 |

Values are means ±1 SD.
$^1$p(0.05 versus controls.
Htwt = ventricular weight;
AN = area of necrosis,
AR = area at risk;
ANAR = necrosis normalized to anatomic risk area;
ARLV = risk zone normalized to total LV area.

These data indicate the utility of compositions containing heparinase for diminishing localized inflammatory responses.

Modifications and variations of the compositions and methods of use of the present invention will be obvious from this detailed description to those skilled in the art. Such modifications are intended to come within the scope of the following claims.

What is claimed is:

1. A method to decrease a localized inflammatory response in a tissue of a patient following surgery, comprising administering to said patient before or simultaneously with surgery at least one heparinase enzyme, wherein said heparinase enzyme decreases said localized inflammatory response in the tissue of the patient.

2. The method of claim 1, wherein said heparinase enzyme is provided with a pharmaceutically acceptable carrier.

3. The method of claim 2, wherein said pharmaceutically acceptable carrier is saline.

4. The method of claim 1, wherein said heparinase enzyme is administered to said patient locally.

5. The method of claim 1, wherein said heparinase enzyme is administered to said patient by perfusion, infusion, or injection.

6. A method of reducing inflammation after transplantation in a patient, comprising perfusing a donor organ to be transplanted in the patient with a heparinase enzyme prior to transplantation.

7. The method of claim 2, wherein said heparinase enzyme is expressed from a recombinant nucleotide sequence in *Escherichia coli, Flavobacterium heparinum,* or an organism in which said enzyme does not naturally occur.

8. The method of claim 2, wherein said heparinase enzyme is heparinase III.

* * * * *

UNITED STATES PATENT AND TRADEMARK OFFICE
CERTIFICATE OF CORRECTION

PATENT NO. : 7,264,799 B2 Page 1 of 1
APPLICATION NO. : 11/357967
DATED : September 4, 2007
INVENTOR(S) : Bennett et al.

It is certified that error appears in the above-identified patent and that said Letters Patent is hereby corrected as shown below:

On the Title Page:

At field (*), add "This patent is subject to a terminal disclaimer."

Signed and Sealed this

Sixth Day of January, 2009

JON W. DUDAS
*Director of the United States Patent and Trademark Office*